(12) United States Patent
Yamamoto et al.

(10) Patent No.: US 7,456,132 B2
(45) Date of Patent: Nov. 25, 2008

(54) PHENOL COMPOUND, REVERSIBLE THERMOSENSITIVE RECORDING MEDIUM, REVERSIBLE THERMOSENSITIVE RECORDING LABEL, REVERSIBLE THERMOSENSITIVE RECORDING MEMBER, IMAGE-PROCESSING APPARATUS AND IMAGING-PROCESSING METHOD

(75) Inventors: Satoshi Yamamoto, Numazu (JP); Kyoji Tsutsui, Mishima (JP); Hiromi Furuya, Sunto (JP); Kyohji Okada, Fuji (JP); Kunio Hayakawa, Mishima (JP); Shinya Kawahara, Numazu (JP); Hitoshi Shimbo, Sunto (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 11/572,058

(22) PCT Filed: Jul. 12, 2005

(86) PCT No.: PCT/JP2005/013224

§ 371 (c)(1),
(2), (4) Date: May 2, 2007

(87) PCT Pub. No.: WO2006/006725

PCT Pub. Date: Jan. 19, 2006

(65) Prior Publication Data

US 2007/0225161 A1    Sep. 27, 2007

(51) Int. Cl.
*B41M 5/333* (2006.01)

(52) U.S. Cl. .................. 503/201; 428/64.4; 503/216
(58) Field of Classification Search .................. None
See application file for complete search history.

(56) References Cited

FOREIGN PATENT DOCUMENTS

| JP | 60 193691 | 10/1985 |
|---|---|---|
| JP | 61 237684 | 10/1986 |
| JP | 62 138556 | 6/1987 |
| JP | 62 138568 | 6/1987 |

(Continued)

*Primary Examiner*—Bruce H Hess
(74) *Attorney, Agent, or Firm*—Oblon, Spivak, McClelland, Maier & Neustadt, P.C.

(57) ABSTRACT

The present invention provides a reversible thermosensitive recording medium including a support and a thermosensitive recording layer thereon, in which the thermosensitive recording layer comprises an electron-donating coloring compound and an electron-accepting compound, and the thermosensitive recording layer is capable of forming a relatively developed condition and a relatively erased condition depending on at least one of the difference of heating temperatures and the difference of cooling rates following to heating, and in which the electron-accepting compound comprises a phenol compound represented by the General Formula (1):

General Formula (1)

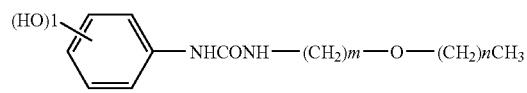

where, in the General Formula (1) "l" represents an integer of 1 to 3, "m" represents an integer of 1 or more, and "n" represents an integer of 7 or more.

21 Claims, 6 Drawing Sheets

FOREIGN PATENT DOCUMENTS

| | | |
|---|---|---|
| JP | 62 140881 | 6/1987 |
| JP | 10 95175 | 4/1988 |
| JP | 63 107584 | 5/1988 |
| JP | 63 173684 | 7/1988 |
| JP | 2 188293 | 7/1990 |
| JP | 2 188294 | 7/1990 |
| JP | 4 78573 | 3/1992 |
| JP | 5 124360 | 5/1993 |
| JP | 6 210954 | 8/1994 |
| JP | 8 301838 | 11/1996 |
| JP | 10 67177 | 3/1998 |
| JP | 11 28867 | 2/1999 |
| JP | 11 349553 | 12/1999 |
| JP | 2000 141893 | 5/2000 |

PHENOL COMPOUND, REVERSIBLE THERMOSENSITIVE RECORDING MEDIUM, REVERSIBLE THERMOSENSITIVE RECORDING LABEL, REVERSIBLE THERMOSENSITIVE RECORDING MEMBER, IMAGE-PROCESSING APPARATUS AND IMAGING-PROCESSING METHOD

TECHNICAL FIELD

The present invention relates to a reversible thermosensitive recording medium in which color images may be formed and erased reversibly based on color-developing reactions between electron-donating coloring compounds and electron-accepting compounds by controlling applied thermal energies, and also relates to a reversible thermosensitive recording label, a reversible thermosensitive recording member, an image-processing apparatus and a method which employ the reversible thermosensitive recording medium respectively.

Further, the present invention relates to novel phenol compounds which are useful electron-accepting compounds as a color developer of the reversible thermosensitive recording medium in which color images may be formed and erased reversibly by controlling applied thermal energies.

BACKGROUND ART

Thermosensitive recording media which utilize reactions between electron-donating coloring compounds thereinafter, sometimes referred as "coloring agent" or "leuco dye") and electron-accepting compounds (hereinafter, sometimes referred as "color developer") have been well-known, and have been broadly utilized as output papers of facsimiles, word processors and scientific instrumentation apparatuses, with an advance of office automation, and nowadays in magnetic thermosensitive cards such as a pre-paid card and point card. From an environmental issue, these conventional recording media in practical use are under pressure to review their use and are required to be recycled, and to be used in less amount; however, recorded images cannot be erased, and thus cannot be used repeatedly. In addition, new information is written only to non-recorded portion, and therefore the total areas capable of being recorded are limited. Thus, under the current situation, the amount of information to be recorded is reduced or a new card is issued when area to be recorded is fully occupied. Against the backdrop of waste problem or problem of deforestation, development of reversible thermosensitive recording medium which is rewritable many times had been desired.

From theses demands, various kinds of reversible thermosensitive recording media have been disclosed. For example, Patent Literatures 1 and 2 disclose a reversible thermosensitive recording medium which is a kind of those using polymer, in which physical change, i.e., transparent and white opaque is utilized. Alternatively, there has been proposed a reversible thermosensitive recording medium which is a kind of those using a dye, in which chemical change is newly utilized Specifically, for example, gallic acid is used in combination with phloroglucinol as a color developer (see Patent Literature 3). Such compounds as phenolphthalein and thymolphtalein are used as a color developer (see Patent Literature 4). Homogeneous mixed solution composed of coloring agent, color developer, and carboxylic acid ester are contained in a recording layer (see Patent Literatures 5, 6, and 7). Ascorbic acid derivatives are used as a color developer (see Patent Literature 8). Salts of bis(hydroxyphenyl)acetic acid or gallic acid and higher aliphatic amine are used as a color developer (see Patent Literatures 9 and 10).

Further, Patent Literature 11 discloses a reversible thermosensitive coloring composition and thermosensitive recording medium. In the reversible thermosensitive coloring composition, an organic phosphorus compound, fatty carbonyl acid compound, or phenol compound each containing a long-chain aliphatic hydrocarbon group as a is developing agent is combined with a leuco dye as a coloring agent, thereby allowing coloring and erasing easily depending on the heating and cooling condition. The developed condition and erased condition can be stably maintained at normal temperature and in addition, developing and erasing can be repeated. And then, Patent Literatures 12 and 13 disclose use of a phenol compound containing a long-chain fatty hydrocarbon group which compound has a specific structure.

In the reversible thermosensitive recording medium where these materials are employed, however, there were such problems that the rate of erasing is slow and thus it takes much time to rewrite erasing is inadequate, or thermal stability of color images is low. Further, in recent years, demands for output with mobile devices have been increased. In these mobile devices, usable power supply depends on the capacity of a dry battery or rechargeable battery, and thus rewrite with low energy or in a short time is required.

Therefore, Patent Literature 14 discloses a reversible thermosensitive recording medium in which a specific phenol compound is used, thereby allowing high contrast between developed condition and erased condition, high-speed erasing, and excellent stability of coloring of an image part. In this reversible thermosensitive recording medium in which the phenol compound is used, color images can be erased by means of a heating member such as a hot stamp, heat roller, or ceramic heater. Therefore, the reversible thermosensitive recording medium is suitable for practical use.

However, many of the phenol compounds exemplified in the above-mentioned Patent Literature 14 have high melting point, which requires heating to high temperature when color developing and erasing and thus requires application of high energy. As a result, some problems arise. Specifically, since pulse is required to be applied for a long time during recording, writing speed is slow, and further high temperature causes large damage to the recording medium, inviting occurrence of blowing trace. In addition, the power supply of the recording apparatus becomes large, resulting in larger rewriting apparatus.

Further, as the phenol compound described in the above-mentioned Patent Literature 12, those having relatively low melting point also have been proposed; however, the reversible thermosensitive recording media in which these compounds were employed exhibits satisfactory coloring sensitivity, but the preservability of the images is not satisfactory and thus the reversible thermosensitive recording media had low practical use.

Patent Literature 1
    Japanese Patent Application Laid-Open No. 63-107584

Patent Literature 2
    Japanese Patent Application Laid-Open No. 04-78573

Patent Literature 3
    Japanese Patent Application Laid-Open No. 60-193691

Patent Literature 4
    Japanese Patent Application Laid-Open No 61-237684

Patent Literature 5
  Japanese Patent Application Laid-Open No. 62-138556

Patent Literature 6
  Japanese Patent Application Laid-Open No. 62-138568

Patent Literature 7
  Japanese Patent Application Laid-Open No. 62-140881

Patent Literature 8
  Japanese Patent Application Laid-Open No. 63-173684

Patent Literature 9
  Japanese Patent Application Laid-Open No. 02-188293

Patent Literature 10
  Japanese Patent Application Laid-Open No. 02-188294

Patent Literature 11
  Japanese Patent Application Laid-Open No. 05-124360

Patent Literature 12
  Japanese Patent Application Laid-Open No. 06-210954

Patent Literature 13
  Japanese Patent Application Laid-Open No. 10-95175

Patent Literature 14
  Japanese Patent Application Laid-Open No. 10-67177

DISCLOSURE OF THE INVENTION

An object of the invention is to provide a reversible thermosensitive recording medium which exhibits satisfactory coloring and decoloring sensitivity and excellent heat resistance and preservability of an image part, and reversible thermosensitive recording member, and image-processing apparatus and process which employ the reversible thermosensitive recording medium respectively.

Another object of the invention is to provide a novel phenol compound which is used as a color developer of the reversible thermosensitive recording medium, has high coloring sensitivity, retains stable color developability and erasability, and has excellent preservability.

The present inventors considered that in reversible color developing and erasing phenomenon of the composition which comprises the coloring agent and color developer, balance between ability of the color developer having a long-chain aliphatic group to develop the coloring agent and the cohesive property between molecules, is important. As a result of designing compounds with a variety of structures, synthesizing them, and investigating them, they have found that use of phenol compound having a specific structure as the color developer can solve the above-mentioned problems.

Further, they considered that in order to increase coloring sensitivity, the color developer is required to have a lower melting point. As a result of investigating compounds with a variety of structures, they have found that by providing the phenol compound having a specific structure, the problems can be effectively solved.

The reversible thermosensitive recording medium of the invention comprises a support and a thermosensitive recording layer thereon, wherein the thermosensitive recording layer comprises an electron-donating coloring compound and an electron-accepting compound, and the thermosensitive recording layer is capable of forming a relatively developed condition and a relatively erased condition depending on at least one of the difference of heating temperatures and the difference of cooling rates following to heating, and wherein the electron-accepting compound comprises a phenol compound represented by the following General Formula (1):

General Formula (1)

where in the General Formula (1), "l" represents an integer of 1 to 3, "m" represents an integer of 1 or more, and "n" represents an integer of 7 or more.

In this case, in one aspect, the electron-accepting compound is preferably a phenol compound represented by the following General Formula (2):

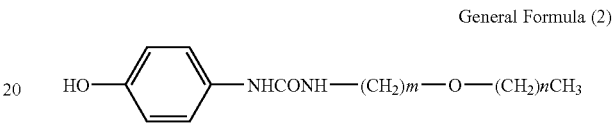

General Formula (2)

where, in the General Formula (2), "m" represents an integer of 1 or more and "n" represents an integer of 7 or more.

Further, in another aspect, preferably, in the General Formulae (1) and (2), the "m" is an integer of 1 or more and the "n" is an integer of 11 to 29, in another aspect, preferably, in the General Formulae (1) and (2), the "m" is an integer of 1 or more and the "n" is an integer of 14 to 22, in another aspect, preferably, in the General Formulae (1) and (2), the "m" is an integer of 3 to 16, in another aspect, preferably, in the General Formulae (1) and (2), the "m" is an integer of 9 to 15.

Furthermore, in another aspect, the thermosensitive recording layer preferably comprises a crosslinked resin, in another aspect, the crosslinked resin preferably has a hydroxyl value of 70 (KOHmg/g) or more, in another aspect, the crosslinked resin preferably has a hydroxyl value of 150 (KOHmg/g) or more, in another aspect, the crosslinked resin is preferably an acrylpolyol resin, in another aspect, the crosslinked resin is preferably crosslinked with an isocyanate compound, in another aspect, preferably, the electron-donating coloring compound is a leuco dye, and the leuco dye has an alkoxyalkyl group in an amino side chain thereof, in another aspect, preferably, the reversible thermosensitive recording medium further comprises a protective layer on the thermosensitive recording layer, wherein the protective layer comprises a crosslinked resin, in another aspect, preferably, the reversible thermosensitive recording medium further comprises a protective layer on the thermosensitive recording layer, wherein the protective layer comprises an ultraviolet-absorbing polymer, in another aspect, the protective layer preferably comprises ultraviolet-absorbing inorganic fine particles, in another aspect, the reversible thermosensitive recording medium is preferably formed into one of a card-like, label-like, sheet-like and roll-like configurations.

The reversible thermosensitive recording label of the invention comprises one of an adhesive layer and a tacky layer, wherein one of the adhesive layer and the tacky layer is disposed on an exposed surface of the reversible thermosensitive recording medium opposite to an exposed surface on which an image is formed.

The reversible thermosensitive recording member of the invention comprises an information-memorizing part and a reversible displaying part, wherein the reversible displaying part comprises the reversible thermosensitive recording medium of the invention.

In this case, in one aspect, the information-memorizing part and the reversible displaying part are preferably integrated, in another aspect, information-memorizing part is preferably selected from the group consisting of a magnetic thermosensitive layer, magnetic stripe, IC memory, optical memory, hologram, RF-ID tag card, disc, disc cartridge and tape cassette.

The image-processing apparatus of the invention comprises at least one of an image-forming unit and an image-erasing unit, wherein images are formed on a reversible thermosensitive recording medium by heating the reversible thermosensitive recording medium in the image-forming unit, images are erased from the reversible thermosensitive recording medium by heating the reversible thermosensitive recording medium in the image-erasing unit, and the reversible thermosensitive recording medium is the reversible thermosensitive recording medium of the invention.

In this case, in one aspect, the image-forming unit is preferably one of a thermal head and a laser irradiation apparatus, in another aspect, the image-erasing unit is preferably one selected from the group consisting of a thermal head, ceramic heater, heat roll, hot stamp, heat block and laser irradiation apparatus.

The image-processing method of the invention comprises: at least one of forming images on a reversible thermosensitive recording medium by heating the reversible thermosensitive recording medium, and erasing images from a reversible thermosensitive recording medium by heating the reversible thermosensitive recording medium wherein the reversible thermosensitive recording medium is the reversible thermosensitive recording medium of the invention.

In this case, in one aspect the image forming is preferably carried out by one of a thermal head and a laser irradiation apparatus, in another aspect the image erasing is preferably carried out by means of one selected from the group consisting of a thermal head, ceramic heater heat roll hot stamp heat block and laser irradiation apparatus in another aspect new images are preferably formed along with erasing images by means of a thermal head.

The phenol compound of the invention is represented by the following General Formula (1):

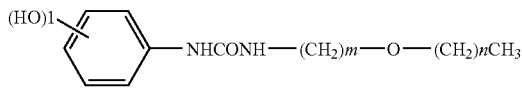

General Formula (1)

where, in the General Formula (1) "l" represents an integer of 1 to 3, "m" represents an integer of 1 or more, and "n" represents an integer of 7 or more.

In this case, in one aspect, the phenol compound is represented by the following General Formula (2):

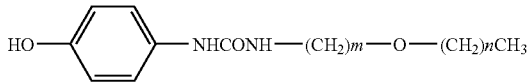

General Formula (2)

where, in the General Formula (2), "m" represents an integer of 1 or more, and "n" represents an integer of 7 or more.

Further, in another aspect, preferably, in the General Formulae (1) and (2), the "m" is an integer of 1 or more and the "n" is an integer of 11 to 29, in another aspect, preferably, in the General Formulae (1) and (2), the "m" is an integer of 1 or more and the "n" is an integer of 14 to 22, in another aspect, preferably, in the General Formulae (1) and (2), the "m" is an integer of 3 to 16, in another aspect, preferably in the General Formulae (1) and (2), the "m" is an integer of 9 to 15.

BEST MODE FOR CARRYING OUT THE INVENTION (Reversible Thermosensitive Recording Medium)

The reversible thermosensitive recording medium according to the invention in which specific phenol compounds are used can form a relatively developed condition and a relatively erased condition depending on the heating temperatures and/or cooling rates following to heating.

The essential color developing and erasing phenomenon, will be described below.

Figure 1:
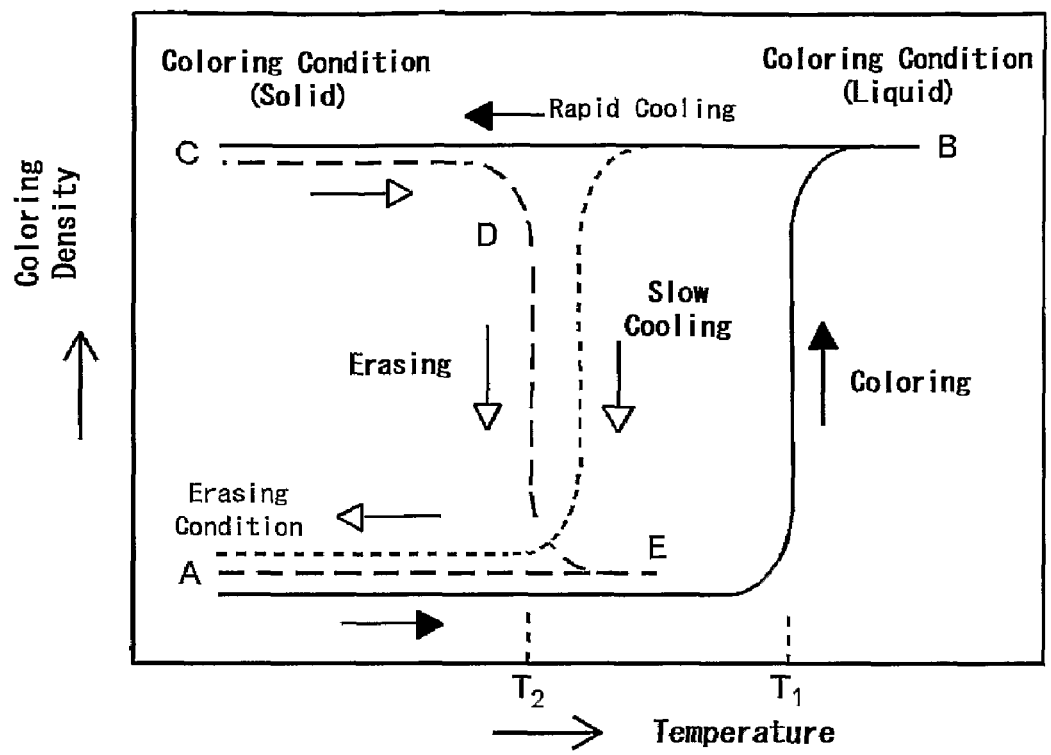
FIG. 1 schematically shows the color developing and erasing property (color developing and erasing phenomena) in an example of the reversible thermosensitive recording medium according to the invention.

Here, FIG. 1 shows the relation between the coloring density and the temperature in the reversible thermosensitive recording medium. When the recording medium is heated from the initial erased condition (A), a leuco dye and color developer are melted at the temperature T1 at which the melting begins, and then the recording medium comes to the melted and developed condition (B), through an occurrence of developing. When cooled rapidly from the melted and developed condition (B), it may be cooled to the room temperature while maintaining the developed condition, thereby a fixed and developed condition (C) emerges. Whether or not the developed condition emerges depends on the cooling rate from the melted condition, and when cooled slowly, the erasing appears during a temperature decreasing process, that is, the initial erased condition (A) or lower density than rapid cooling (C) emerges. On the other hand, when heated again from rapidly cooled coloring condition (C), erasing occurs at a lower temperature T2 than the developing temperature (D to E); when cooled from this temperature, resulting in the initial erased condition (A). Actual developing and erasing temperatures may be selected depending on the application since these temperatures vary with the utilized coloring agent and color developer. Further, the coloring density at the melting condition and the coloring density after the rapid cooling may not necessarily coincide, are different significantly in some cases.

In the reversible thermosensitive recording medium of the invention, the coloring condition (C) obtained through rapid cooling from the melted condition is a condition in which the coloring agent and color developer are blended such that they may react through molecular contact, and the coloring condition is often solid state. In the condition, the coloring agent and color developer are coagulated to represent a coloring condition. It is believed that the formation of the coagulated condition makes the coloring condition stable. On the other hand, in the erased condition, the coloring agent and color developer are in phase separation. It is believed that the molecules of at least one of the compounds assemble to form domains or crystals in the separated condition, and that the coloring agent and color developer are separated and stabilized through the coagulation or crystallization. In the invention, in many cases, the phase separation of the coloring agent and the color developer and also the crystallization of the color developer cause the erasion more perfectly. In the erasion due to slower cooling from the melted condition as well as the erasion due to the heating from the coloring condition as shown in FIG. 1, the coagulated structures are altered depending on the temperatures, resulting in the phase separation and or crystallization of the color developer.

It is believed that the more stable the coagulated condition of the coloring agent and the color developer is, the more stable the stability of the developed state. Thus, it has been considered that associating group which forms hydrogen bonding to be introduced in the molecular structure of the color developer. However, stronger hydrogen bonding of the color developer molecule leads to high melting point of the color developer, and thus the temperature at which coloring starts becomes higher, resulting in the reduced sensitivity characteristics of the recording medium.

In the invention, introduction of a urea group and an ether group into the molecular structure of the color developer and in addition, possession of a long-chain alkyl group leads to satisfactory stability of coloring without higher melting point of the color developer and enabled both of the coloring sensitivity and the preservation stability of an image part.

Here, the phenol compound for use in the invention as the color developer is represented by the following General Formula (1).

General Formula (1)

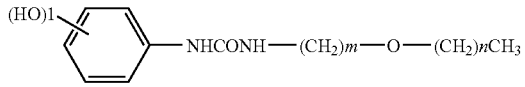

In the General Formula (1), "l" represents an integer of 1 to 3 and the General Formula (1) is represented by the following General Formulae (2) to (8).

General Formula (2)

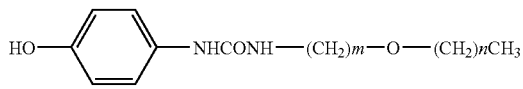

General Formula (3)

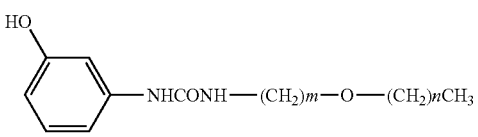

General Formula (4)

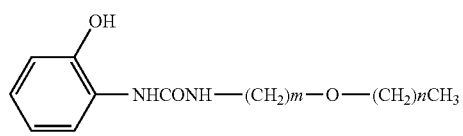

General Formula (5)

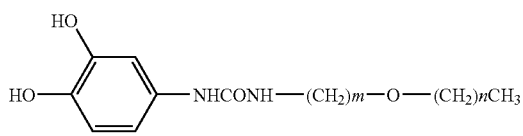

General Formula (6)

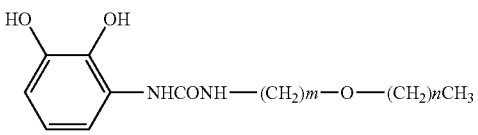

General Formula (7)

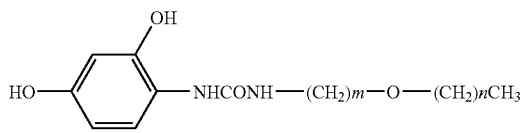

General Formula (8)

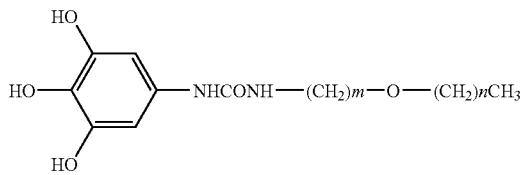

Among the above-mentioned General Formulae (2) to (8), the above-mentioned compound of General Formula (2) is preferably used as those allowing excellent color developing and or erasing property, but nearly comparable results were obtained when the above-mentioned compound of General Formulae (3) to (8) were used.

Further, "m" represents an integer of 1 or more, preferably an integer of 3 to 16, more preferably an integer of 9 to 15. "n" represents an integer of 7 or more, preferably an integer of 11 to 29, more preferably an integer of 14 to 22.

Here, since larger values of the "m" and "n" improve the stabilities of the color optical density, erasing optical density, color images, compounds each having longer chain length give satisfactory recording media. However, on the other hand, longer chain length causes problems in terms of its practical use due to unavailability of raw materials for their high price. Therefore, by using compounds each having chain length corresponding to the total values of "m" and "n", ranging from 10 to 70, preferably 20 to 60, more preferably 30 to 50, satisfactory characteristics of the recording medium such as color optical density, erasing optical density, and stability of images can be achieved, in addition, raw materials are available at relatively low price and resulting recording medium is of high practical use.
The phenol compounds for use in the invention will be exemplified below
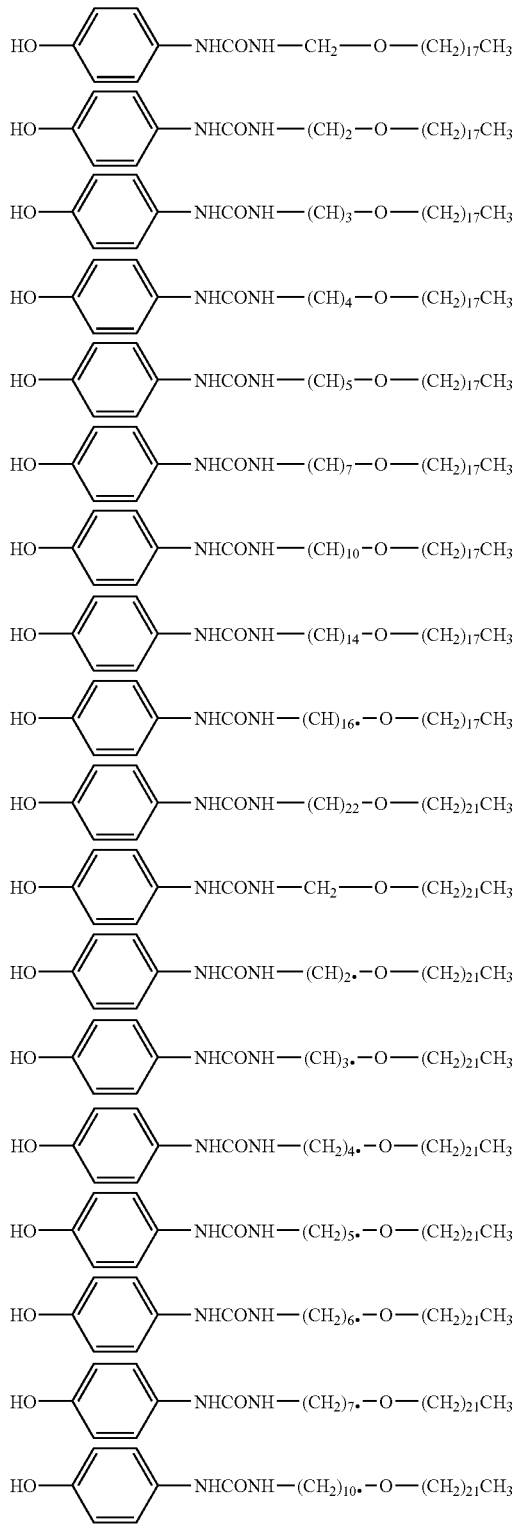
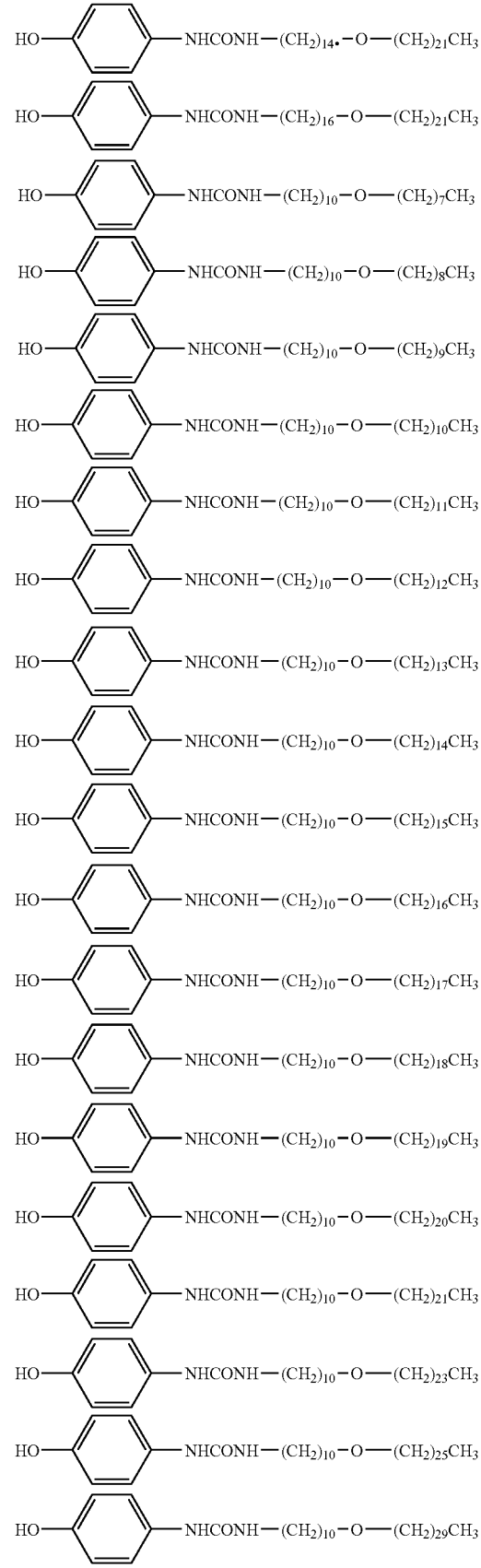

-continued

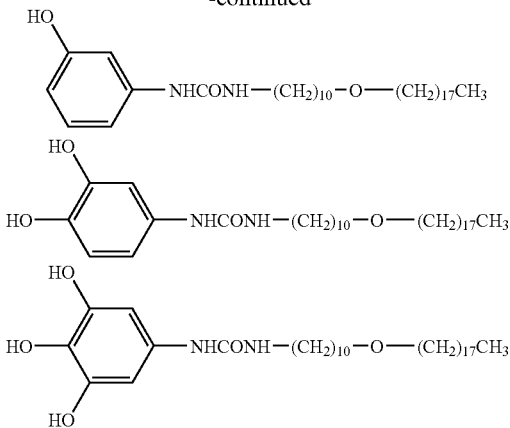

Further, the leuco dyes for use in the invention can be used singly or by mixture and are known precursor dyes such as, for example, phthalide compounds, azaphthalide compounds, and fluoran compounds.

Specific examples of the leuco dyes include the following compounds
2-anilino-3-methyl-6-diethylaminofluoran,
2-anilino-3-methyl-6-(di-n-butylamino)fluoran,
2-anilino-3-methyl-6-(N-n-propyl-N-methylamino)fluoran,
2-anilino-3-methyl-6-(N-isopropyl-N-methylamino)fluoran,
2-anilino-3-methyl-6-(N-isobutyl-N-methylamino)fluoran,
2-anilino-3-methyl-6-(N-n-amyl-N-methylamino)fluoran,
2-anilino-3-methyl-6-(N-sec-butyl-N-methylamino)fluoran,
2-anilino-3-methyl-6-(N-3-ethoxypropyl-N-ethylamino) fluoran
2-anilino-3-methyl-6-(N-tetrahydrofurfuryl-N-ethylamino) fluoran
2-anilino-3-methyl-6-(N-n-amyl-N-ethylamino)fluoran
2-anilino-3-methyl-6-(N-iso-amyl-N-ethylamino)fluoran,
2-anilino-3-methyl-6-(N-n-propyl-N-isopropylamino)-fluoran,
2-anilino-3-methyl-6-(N-cyclohexyl-N-methylamino)-fluoran,
2-anilino-3-methyl-6-(N-ethyl-p-toluidino)fluoran,
2-anilino-3-methyl-6-(N-methyl-p-toluidino)fluoran,
2-(3-toluidino)-3-methyl-6-diethylaminofluoran,
2-(m-trichloromethylanilino)-3-methyl-6-diethylaminofluoran
2-(m-trifluoromethylanilino)-3-methyl-6-diethylaminofluoran,
2-(m-trichloromethylanilino)-3-methyl-6-(N-cyclohexyl-N-methylamino) fluoran
2-(2,4-dimethylanilino)-3-methyl-6-diethylaminofluoran
2-(N-ethyl-p-toluidino)-3-methyl-6-(N-ethylanilio)fluoran,
2-(N-ethyl-p-toluidino)-3-ethyl-6-(N-propyl-p-toluidino) fluoran,
2-anilino-6-(N-n-hexyl-N-ethylamino)fluoran,
2-(o-chloroanilino)-6-diethylaminofluoran,
2-(o-chloroanilino)-6-dibutylaminofluoran,
2-(m-trifluoromethylanilino)-6-diethylaminofluoran,
2,3-dimethyl-6-dimethylaminofluoran,
3-methyl-6-(N-ethyl-p-toluidino)fluoran,
2-chloro-6-diethylaminofluoran.
2-bromo-6-diethylaminofluoran,
2-chloro-6-dipropylaminofluoran, 3-chloro-6-cyclohexylaminofluoran,
3-bromo-6-cyclohexylaminofluoran,
2-chloro-6-(N-ethyl-N-isoamylamino)fluoran
2-chloro-3-methyl-6-diethylaminofluoran,
2-anilino-3-chloro-6-diethylaminofluoran-1.
2-(o-chloroanilino)-3-chloro-6-cyclohexylaminofluoran,
2-(m-trifluoromethylanilino)-3-chloro-6-diethylaminofluoran,
2-(2,3-dichloroanilino)-3-chloro-6-diethylaminofluoran,
1,2-benzo-6-diethylaminofluoran,
3-diethylamino-6-(m-trifluoromethylanilino)fluoran,
3-(1-ethyl-2-methylindole-3-yl)-3-(2-ethoxy-4-diethylaminophenyl)-4-azaphthalide,
3-(1-ethyl-2-ethylindole-1-yl)-3-(2-ethoxy-4-diethylaminophenyl)-7-azaphthalide,
3-(1-octyl-2-methylindole-3-yl)-3-(2-ethoxy-4-diethylaminophenyl)-4-azaphthalide,
3-(1-ethyl-2-methylindole-3-yl)-3-(2-ethyl-4-diethylaminophenyl)-4-azaphthalide,
3-(1-ethyl-2-methylindole-3-yl)-3-(2-methyl-4-diethylaminophenyl)-7-azaphthalide,
3-(1-ethyl-2-methylindole-3-yl)-3-(4-diethylaminophenyl)-4-azaphthalide,
3-(1-ethyl-2-methylindole-3-yl)-3-(4-N-n-amyl-N-methylaminophenyl)-4-azaphthalide,
3-(1-methyl-2-methylindole-3-yl)-3-(2-hexyloxy-4-diethylaminophenyl)-4-azaphthalide,
3,3-bis(2-ethoxy-4-diethylaminophenyl)-4-azaphthalide, and
3,3-bis(2-ethoxy-4-diethylaminophenyl)-7-azaphthalide.

Among these, 2-anilino-3-methyl-6-(N-3-ethoxypropyl-N-ethylamino)fluoran and the like are particularly preferred since a structure in which the amino side chain at the 6-position of fluoran has an ether group enhances erasing performance of images. Examples of the structure of the amino side chain having an ether group include N-ethyl-N-methoxymethylamino, N-ethoxymethyl-N-ethylamino, N-3-ethoxypropyl-N-ethylamino, N,N,-di(3-ethoxypropyl)amino, N-ethyl-N-3-octadecyl oxypropylamino and the like.

Appropriate range of the blending ratio of the leuco dye and the color developer varies depending on the combinations of the utilized compounds. Preferably, the mol ratio of the color developer to the coloring agent is 0.1 to 20, more preferably 0.2 to 10. The color developer amount of over or under this range may result in a lower coloring density. Further, the leuco dye and color developer may be utilized in an encapsulated condition.

The binder resin, which is utilized for forming a thermosensitive recording layer together with the leuco dye and the color developer, may be properly selected depending on the application without particular limitations. Examples of the binder resin include polyvinyl chloride, polyvinyl acetate, vinylchloride-vinylacetate copolymers, ethylcellulose, polystyrenes, styrene copolymers, phenoxy resins, polyesters, aromatic polyesters, polyurethanes polycarbonates, polyester acrylates, polyester methacrylate, acrylic acid copolymers, maleic acid copolymers, polyvinylalcohols, modified polyvinylalcohols, hydroxylethylcellulose, carboxymethylcellulose, and starch. These binder resins serve to prevent the deviation of the respective materials in the composition due to heating for the recording erasures thereby to maintain the uniformly dispersed condition. Accordingly, the binder resin is preferred to be highly heat-resistant. The binder resin may be crosslinked by means of heating, ultra-violet irradiation, electron beam and the like.

The thermosensitive recording layer preferably comprises a crosslinked resin. Specific examples of the crosslinked resin include such resins, having a group reactive with a crosslinking agent, as acrylpolyol resins, polyesterpolyol resins, polyurethanepolyol resins, phenoxy resins, polyvinylbutyral resins, celluloseacetate propionate resins, and celluloseacetate butyrate resins, and copolymer resins between a monomer having a group reactive with a cross-linking agent and another monomer, but in the invention, the crosslinked resin is not limited to these compounds.

Further, the thermosensitive recording layer preferably comprises a crosslinked resin having a hydroxyl value of 70 (KOHmg/g) or more, and as the resin having a hydroxyl value of 70 (KOHmg/9) or more, acrylpolyol resins, polyesterpolyol resins, polyurethanepolyol resins, or the like are employed, but, in particular, the acrylpolyol resins are preferably employed for satisfactory stability of coloring and satisfactory erasability. The hydroxyl value is 70 (KOHmg/g) or more and particularly preferably 90 (KGHmg/g) or more. The level of the hydroxyl value is related to the crosslinking density; therefore it affects the chemical resistance, properties and the like of the coating. The present inventors have found that the resins having a hydroxyl value of 70 (KOHmg/g) or more enhances the durability, surface hardness of the coating, and cracking resistance. Whether or not the resin having a hydroxyl value of 70 (KOHmg/g) or more in one reversible thermosensitive recording material can be confirmed, for example, by analyzing the amount of remaining hydroxyl groups and the amount of ether bond.

Further, it has found that if the cross inked resin has a hydroxyl value of 150 (KOHmg/g) or more, preferably 170 (KOHmg/g) to 350 (KOHmg/g) more preferably 200 (KOHmg/g) to 300 (KOHmg/g), the crosslinking density is further improved, bringing about structural stability. Therefore, erasing performance of a coloring object is improved and image can be erased in a shorter time during which the coloring object is exposed to erasing temperature.

The acrylpolyol resins have different characteristics depending on their composition, as a monomer having hydroxyl group, hydroxyethylacrylate (HEA) hydroxy-propylacrylate (HPA), 2-hydroxyethylmethacrylate (HEMA), 2-hydroxypropylmethacrylate (HPMA), 2-hydroxybutylmonoacrylate (2-HBA), 1,4-hydroxybutylmonoacrylate (1-HBA), or the like is used Among these, the monomer having a primary hydroxyl group such as 2-hydroxyethylmethacrylate is suitably utilized, in light of superior cracking resistance and durability of the coating.

As a curing agent, examples include conventional isocyanate compounds, amine compounds, phenol compounds, epoxy compounds and the like. Among these compounds, isocyanate compound is suitably utilized. The isocyanate compound used here may be selected from various derivatives of known isocyanate monomer such as urethane-modified, allophanate-modified, isocyanurate-modified, buret-modified, and carbodiimide-modified compounds, and blockedisocyanate compounds. Examples of the isocyanate monomer, which may yield the modified compounds, include tolylenediisocyanate (TDI), 4,4-diphenylmethane diisocyanate (MDI), xylylenediisocyanate (XDI), naphthylenediisocyanate (NDI), paraphenylenediisocyanate (PPDI), tetramethylxylylenediisocyanate (TMXDI), hexamethylenediisocyanate (HDI), dicyclohexylmethanediisocyanate (HMDI), isophoronediisocyanate (IPDI), lysinediisocyanate (LDI), isopropylidenebis(4-cyclohexylisocyanate) (IPC), cyclohexyldiisocyanate (CHDI), and tolidinediisocyanate (TODI), but in the invention, the curing agent is not limited to these compounds.

Further, as the crosslinking promoter, a catalyst may be employed which is utilized in general for such reaction. Examples of the crosslinking promoter include tertiary amines such as 1,4-diaza-bicyclo(2,2,2)octane, and metal compounds such as organic tin compounds. Further, all of the introduced curing agent may not so necessarily react for the crosslinking.

That is, the curing agent may be remained in unreacted condition. Such crosslinking reaction may progress with time; therefore, the presence of unreacted curing agent does not indicate that the crosslinking reaction has not progressed at all, nor suggests that the crosslinked resins do not exist, even if the unreacted curing agent is detected. Further, an immersion test of polymer into a solvent with a high solubility may be employed for distinguishing whether or not the polymer is in crosslinked condition. That is, the non-crosslinked polymer cannot remain in the solute since such polymer dissolves into the solvent, an analysis may be properly carried out for examining the existence of the polymer in the solute.

Further, according to the invention, the recording layer may contain, together with the above-mentioned color developer and the leuco dye, a color developing and erasing controlling agent having straight-chain hydrocarbon group and hydrogen-containing groups such as an amide group and a urea group. Thus, satisfactory preservation stability of color images can be achieved, at the same time, erasability during erasing is also improved and satisfactory erasing property can be achieved.

Moreover, according to the invention, a protective layer which contains the crosslinked resin, may be provided on the thermosensitive recording layer. The resin for use in the protective layer include, as in the above-mentioned recording layer, thermosetting resins, UV curable resins, electron beam curable resins.

Particularly preferably, the resins for use in the protective layer are ultraviolet-absorbing polymers having an ultraviolet-absorbing group in the molecular structure thereof.

As the ultraviolet-absorbing polymer, polymers composed of a monomer having an ultraviolet-absorbing group and a monomer having a functional group capable of being crosslinked are preferably used. As the monomer having an ultraviolet-absorbing group, monomers having benzotriazole skeleton such as (2'-Hydroxy-5'-methacryloxyethylphenyl)-2H-benzotriazole, 2-(2'-Hydroxy-5'-methylphenyl)benzotriazole, and 2-(2'-Hydroxy-3-ω-butyl-5'-methylphenyl)-5-chlorobenzotriazole are particularly preferably used.

Further, examples of the monomer containing a functional group include 2-isopropenyl-2-oxazoline, 2-aziridinylethyl (meth)acrylate, methacylic acid, glycidyl(meth)acrylate, hydroxylethyl(meth)acrylate, hydroxylpropyl(meth)acrylate, dimethylaminoethyl(meth)acrylate, diethylaminoethyl(meth)acrylate, t-butylaminoethyl(meth)acrylate, tetrahydrofurfuryl(meth)acrylate, among these, hydroxylethyl(meth)acrylate, hydroxylpropyl(meth)acrylate, and the like are particularly preferably used.

Further in order to enhance coating strength and heat resistance, the following monomer may be copolymerized with copolymers of the monomer containing an ultraviolet-absorbing group and the monomer containing a functional group. Examples thereof include monomers such as styrene, styrene-butadiene, styrene-isobutylene, ethylenevinyl acetate, vinyl acetate methacrylonitrile vinyl alcohol, vinyl pyrrolidone, acrylonitrile, and methacrylonitrile; (meth) acrylic esters, which do not contain the functional group such as acrylic acid methyl(meth)acrylate, ethyl(meth)acrylate, propyl(meth)acrylate, butyl(meth)acrylate, isobutyl(meth)acrylate, t-butyl(meth)acrylate, ethylhexyl(meth)acrylate, octyl(meth)acrylate, isodecyl(meth)acrylate, lauryl(meth)acrylate, lauryl tridecyl(meth)acrylate, tridecyl(meth)acrylate, cetylstearyl(meth)acrylate, stearyl(meth)acrylate, cyclohexyl(meth)acrylate, and benzyl(meth)acrylate; monomers which have two or more polymerizable double bond in one molecule thereof, such as ethylene di(meth)acrylate, diethylene glycol di(meth)acrylate, triethylene glycol di(meth)acrylate, tetraethylene glycol di(meth)acrylate, decaethylene glycol di(meth)acrylate, pentacontahecta ethylene glycol di(meth)acrylate, butylene di(meth)acrylate, pentaerythritol tetra(meth)acrylate, trimethylolpropane tri(meth) acrylate, pentadeca ethylene glycol di(meth)acrylate, and diethylene glycol phthalate di(meth)acrylate, but the monomer to be copolymerized is not particularly limited to these. Among these, styrene, methyl(meth)acrylate, ethyl(meth) acrylate, propyl(meth)acrylate, butyl(meth)acrylate, isobutyl (meth)acrylate t-butyl(meth)acrylate and the like are particularly suitably used. Further, two or more thereof can be used in combination according to necessary.

From the above description, specific suitable examples of the polymer having ultraviolet-absorbing structure, which is used in the invention include copolymers composed of 2-(2'-hydroxy-5'-methacryloxyethyl phenyl)-2H-benzotriazole, 2-hydroxyethyl methacrylate and styrene; copolymers composed of 2-(2'-hydroxy-5'-methylphenyl)benzotriazole, 2-hydroxypropyl methacrylate and methyl methacrylate; and the like, but the polymer having ultraviolet-absorbing structure is not particularly limited to these.

Further, according to the invention, the protective layer may comprise ultraviolet-absorbing inorganic fine particles.

The inorganic pigment is not particularly limited provided that the pigment has an average particle size of 0.1 μm or less. Examples of such inorganic pigment include such metal oxides and metal complex oxides as zinc oxide, indium oxide, alumina, silica, zirconium oxide, tin oxide, cerium oxide, iron oxide, antimony oxide, barium oxide, calcium oxide, bismuth oxide, nickel oxide, magnesium oxide, chromium oxide, manganese oxide, tantalum oxide, niobium oxide, thorium oxide, hafnium oxide, molybdenum oxide, iron ferrite, nickel ferrite, cobalt ferrite, barium titanate and potassium titanate, such metal sulfides or sulfates as zinc sulfide and barium sulfate, such metal carbides as titanium carbide, silicon carbide, molybdenum carbide, tungsten carbide and tantalum carbide, and such metal nitride as aluminum nitride, silicone nitride, boron nitride, zirconium nitride, vanadium nitride, titanium nitride, niobium nitride, and gallium nitride.

Among these, pigments having absorption end in the wavelength region of 400 nm or less are particularly preferred.

These pigments are classified into two groups: (A) pigments having absorption end in the UV-A region of the spectrum, i.e., wavelength of 320 nm to 400 nm, (B) inorganic pigments having absorption end in the shorter wavelength region than the UV-A region. In the invention, the inorganic pigment (A) or inorganic pigment (B) can be used alone, but use of the inorganic pigment (A) and inorganic pigment (B) in combination makes the effect of the invention more remarkable. When the inorganic pigment (A) or inorganic pigment (B) is used alone, these pigments may be contained in an intermediate layer or the protective layer. Further, when the inorganic pigment (A) and inorganic pigment (B) is used in combination, these pigments may be contained in the intermediate layer or the protective layer at the same time, but the inorganic pigment (A) and inorganic pigment (B) may be separately contained in the intermediate layer or the protective layer. In this case, the inorganic pigment (A) may be contained in the intermediate layer and the inorganic pigment (B) may be contained in the protective layer, by which the effect of the invention can be achieved more remarkably.

Specific examples of the above-noted inorganic pigment (A) include zinc sulfide, titanium oxide, indium oxide, cerium oxide, tin oxide, molybdenum oxide, zinc oxide, and gallium nitride.

Further, specific examples of the inorganic pigment (B) include silica, alumina, silica-alumina, antimony oxide, magnesium oxide, zirconium oxide, barium oxide, calcium oxide, strontium oxide, silicone nitride, aluminum nitride, boron nitride, and barium sulfate.

Further, in the invention, inorganic or organic filler, lubricant, etc. which are used in this kind of recording medium may be used in the protective layer.

The support of the reversible thermosensitive recording medium of the invention may be, for example, paper, resin film, PET film, synthetic paper, metal foil, glass, or complexes thereof, and may be those capable of retaining the thermosensitive recording layer. Further, those having the thickness according to necessity can be used alone or by, for example, bonding. Specifically, supports having any thickness from about a few micrometers to about a few millimeters, preferably 60 μm to 150 μm, may be used.

Further, when an under layer is provided on these supports, disposing the under layer via an adhesion layer prevents occurrence of crack and improves generation of a burr.

The adhesion layer can be formed, for example, by the similar coating method as that employed in the above-mentioned respective layers.

The reversible thermosensitive recording medium may be formed into various shapes depending on the application such as card-like, sheet-like, label-like, or roll-like shape.

The applications of the recording medium formed into a card-like shape include prepaid card, point card and also credit card. The recording medium formed into a sheet-like shape of normal document size such as A4 size may be applied broadly into temporary output applications such as normal document, instructing letter for process management, circulation document, and conference data, needless to say trial printings, owing to the wider printable area than the card-like size when an printing-erasing apparatus is introduced.

The recording medium formed into a roll-like shape may be applied for display board, notice plate and electronic white board by being integrated into an instrument with a printing-erasing part. Such display instruments may be appropriately utilized in a clean room since dusts and contaminants are not emitted.

(Reversible Thermosensitive Recording Member)

According to the reversible thermosensitive recording member of the invention, the reversibly displayable thermosensitive layer and the information-memorizing part are provided in one card (integrated), and a part of the memorized information of the information-memorizing part is displayed on the thermosensitive layer, thereby the owner of the card may be convenient in that the information can be confirmed by only viewing the card without a particular device. Further, in the case that the content of the information-memorizing part is overwritten, the recording medium may be repeatably utilized by overwriting the display of the thermosensitive recording part.

The member comprising the information-memorizing part and the reversible displaying part may be classified in the following two types (1) A part of the member comprising the information-memorizing part is utilized as a support of the reversible thermosetting recording medium and the thermosensitive layer is disposed on the support directly.

(2) A thermosensitive layer is disposed separately on a support to form a reversible thermosensitive recording medium, and the support is adhered to the member comprising the information-memorizing part.

In these cases of (1) and (2), the position of the disposed information-memorizing part may be the opposite side of the thermosensitive layer on the support of the recording medium, between the support and the thermosensitive layer, or on a part of the thermosensitive layer, provided that the information-memorizing part and the reversible displaying part are designed to perform their functions.

The information-memorizing part is not particularly limited, but for example, may be preferably formed of a magnetic thermosensitive layer, magnetic stripe, IC memory, optical memory, RF-ID tag card, hologram, and the like. In the sheet medium of which the size is over the card size, the IC memory and RF-ID tag are preferably employed. By the way, the RF-ID tag is composed of an IC chip and an antenna connected to the IC chip.

The magnetic thermosensitive layer may be formed by coating on a support a coating material comprising conventional iron oxide, barium ferrite etc. and vinylchloride resins, urethane resins, nylon resins etc., or by vapor deposition, spattering etc. without using resins. The magnetic thermosensitive layer may be provided on the face of the support opposite to the thermosensitive layer, between the support and the thermosensitive layer, or on a part of the thermosensitive layer. Further, the reversible thermosensitive material for displaying may be employed for the memorizing part in a form of barcode, two dimensional code and the like. The magnetic recording and IC is more preferable among these.

As for the hologram, the rewritable type is preferred, for example, the rewritable hologram in which coherent light is written on a liquid crystal film of azobenzene polymer is exemplified.

The member comprising the information recording part typically includes a card, disc, disc cartridge, and tape cassette. Specifically, examples of the member include a thicker card such as IC card and optical card; disc cartridge containing an information-rewritable disc such as flexible disk, optical magnetic disc (MD) and DVD-RAM; disc in which disc cartridge is not utilized, e.g. CD-RW; overwrite type disc such as CD-R; optical information recording medium with phase-changing recording material (CD-RW); and video cassette.

Further the member comprising the information-memorizing part and the reversible displaying part may exhibit remarkably increased availability. That is, in case of card for example, the owner of the card can confirm the information only by viewing the card without a particular device through displaying on the thermosensitive layer a part of the information memorized in the information recording part.

The information-memorizing part may be properly selected depending on the application without particular limitations, provided that the necessary information may be recorded, for example, a magnetic recording contact type IC, non-contact type IC, and optical memory are exemplified.

The magnetic thermosensitive layer may be formed by coating on a support a coating material comprising metallic compounds such as conventional iron oxide, barium ferrite etc. and vinylchloride resins, urethane resins, nylon resins etc., otherwise by vapor deposition spattering etc. using the metallic compounds without using resins. Further, the thermosensitive layer of the reversible thermosensitive recording medium for displaying may be employed for the memorizing part in a form of barcode two dimensional code and the like.

More specifically, the reversible recording medium of the invention may be appropriately employed for the reversible thermosensitive recording label, reversible thermosensitive recording member image-processing apparatus, and image-processing method. In the invention, "surface of the reversible thermosensitive recording medium" means the surface on the side of the thermosensitive layer, which surface means not only that of the protective layer, but also all of or part of the surface which contact with the thermal head during the printing and erasing, such as the surface of printing layer or OP layer.

(Reversible Thermosensitive Recording Label)

The reversible thermosensitive recording label comprises one of an adhesive layer and tacky layer on an exposed surface of the reversible thermosensitive recording medium opposite to the exposed surface on which an image is formed (in the case that the thermosensitive layer exists on the support an exposed surface of the support opposite to the surface on which an image is formed) and the other layers properly selected depending on the necessity. Further, in the case that the support of the reversible thermosensitive recording medium is of heat fusion, the adhesive layer or tacky layer on a surface of the support opposite to the surface on which an image is formed.

The shape, configuration, size and the like of the adhesive layer or tacky layer may be properly selected depending on the application without particular limitations. The shape may be sheet-like or film-like; the configuration may be of single layer or laminated layers; and the size may be larger or smaller than the thermosensitive layer.

The material of the adhesive layer or tacky layer may be properly selected depending on the application without particular limitations. Examples of the material include urea resins, melamine resins, phenolic resins, epoxy resins, polyvinyl acetate resins, vinyl acetate-acrylic copolymers, ethylene-vinyl acetate copolymers, acrylic resins, polyvinyl ether resins, vinyl chloride-vinyl acetate copolymers polystyrene resins, polyester resins, polyurethane resins, polyamide resins, chlorinated polyolefin resins polyvinyl butyral resins, acrylic ester copolymers, methacrylic ester copolymers, natural rubber, cyanoacrylate resins, silicone resins. These may be used alone or in combination. Further the material may be of hot-melt type, and may be used either with a disposable release paper or without a disposable release paper.

The reversible thermosensitive recording label is normally utilized in a configuration laminated to a substrate sheet such as a card, in which the reversible thermosensitive recording label may be laminated on the entire or part of the substrate sheet, or on one side or both sides.

The shape, configuration, size and the like of the substrate sheet may be properly selected depending on the application without particular limitations. The shape may be plate-like or the like; the configuration may be of single layer or laminated layers; and the size may be properly selected depending on the size of the reversible thermosensitive recording medium. For example, the substrate may be a sheet or laminated body formed of chlorine-containing polymers, polyester resins, biodegradable plastic resins and the like.

The chlorine-containing polymer may be properly selected depending on the application without particular limitations; examples of the polymer include polyvinyl chloride, vinyl chloride-vinyl acetate copolymers, vinylchloride-vinylacetate-vinylalcohol copolymers, vinylchloride-vinylacetate-maleicacid copolymers, vinylchloride-acrylate copolymers, polyvinylidenechloride, vinylidenechloride-vinylchloride copolymers, and vinylidenechloride-acrylonitrile copolymers Examples of the polyester resins include polyethylene terephthalate (PET), polybutylene terephthalate (PET), alternatively condensed esters of acid ingredients such as terephthalic acid, isophthalic acid, and alcohol ingredients such as ethylene glycol, cyclohexanedimethanol (e.g. PETS, trade name by Eastman Chemical Co.).

Examples of the biodegradable plastic resins include natural polymer resins comprising polylactic acid, starch, denaturated polyvinyl alcohol and the like, and microbiological product resins including beta-hydroxybutyric acid and beta-hydroxyvaleric acid.

Further, the substrate may be synthetic resin sheet or paper formed of polyacetate resins, polystyrene (PS) resins, epoxy resins, poly-vinylchloride (PVC) resins, polycarbonate (PC) resins, polyamide resins, acryl resins, silicone resins and the like. These materials may be properly combined or laminated.

As for the laminated body, the body comprising a core sheet formed of laminated two sheets of white polyvinyl chloride resin of 250 μm thick, and two laminated over sheet of transparent polyvinyl chloride resin of 100 μm thick on the both surfaces of the core sheet may be exemplified. Also the laminate body comprising a core sheet formed of laminated two sheets of white PETG of 250 μm thick, and two laminated over sheet of transparent PETG of 100 μm thick on the both surfaces of the core sheet may be exemplified.

When one of adhesive layer and tacky layer exist in the reversible thermosensitive recording label, the reversible thermosensitive recording label may be affixed on an entire or part of a thicker substrate such as polyvinylchloride card with magnetic stripe to which the thermosensitive layer is usually difficult to be affixed, thereby a part of the information memorized in magnetic may be displayed.

The reversible thermosensitive recording label may be an alternative to a thicker card such as IC card and optical card, flexible disc, disc cartridge containing rewritable disc such as optical magnetic recording disc (MD) and DVD-RAM, disc without disc cartridge such as CD-RW, write-once disc such as CD-R, optical information recording medium (CD-RW) based on phase-change recording material, and display label on video cassette.

Figure 2:
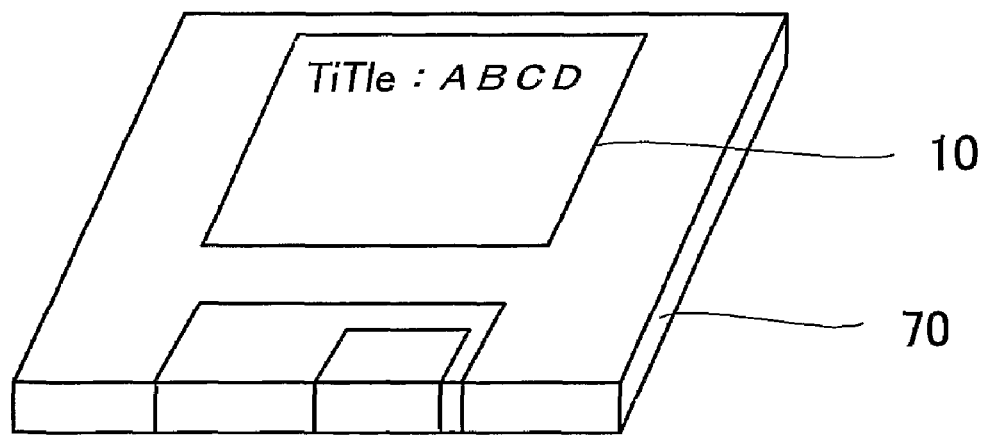
FIG. 2 is a diagram exemplifying a configuration, in which a reversible thermosensitive recording label is laminated on an MD disc cartridge.

FIG. 2 exemplifies the reversible thermosensitive recording label 10 of the invention affixed to MD disc cartridge 70. In this case, such application is allowable that the displayed content is automatically altered depending the alternation of the memorized content in the MD. Further, in a case of disc without disc cartridge such as CD-RW, the reversible thermosensitive recording label of the invention may be directly affixed to the disc.

Figure 3:
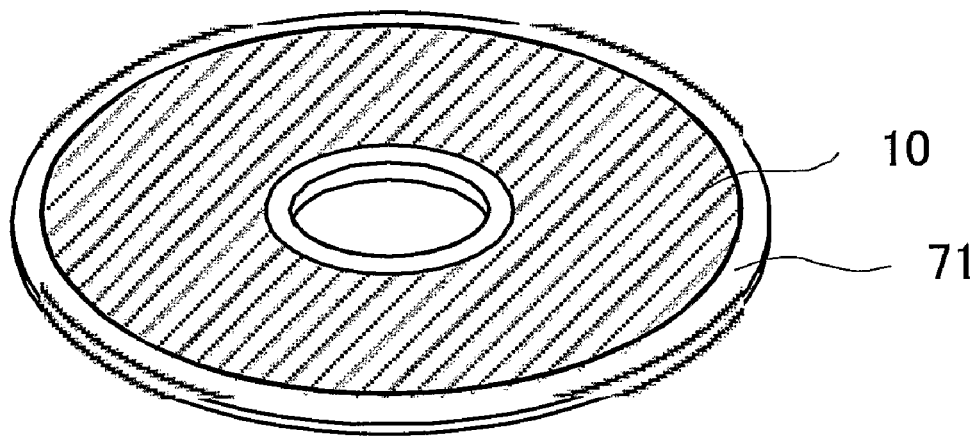
FIG. 3 is a diagram exemplifying a configuration, in which a reversible thermosensitive recording label is laminated on a CD-RW.
Figure 4:
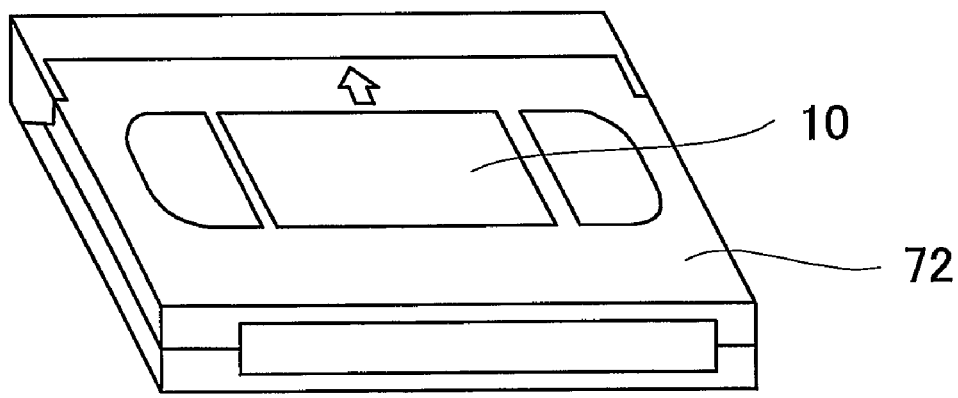
FIG. 4 is a diagram exemplifying a configuration in which a reversible thermosensitive recording label is employed on a video cassette as a display label.

FIG. 3 exemplifies the reversible thermosensitive recording label 10 of the invention affixed to CD-RW 71. In this case, the reversible thermosensitive recording label is affixed on a write-once disc such as CD-R in place of CD-RW, then a part of the memorized information in the CD-R may be rewritten and displayed FIG. 4 shows an example of the cases where the reversible thermosensitive recording label 10 of the invention is affixed to a video cassette 72. In this case, such application is allowable that the display is automatically altered depending on the change of the memories in the video cassette.

(Image-Processing Method and Image-Processing Apparatus)

The image-processing apparatus of the invention comprises at least one of an image-forming unit and image-erasing unit, and the other unit properly selected depending on the necessity such as conveying unit controlling unit and the like.

The image-processing method of the invention performs at least one of forming images and erasing images by heating the reversible thermosensitive recording medium and comprises the other operations properly selected depending on the necessity such as conveying, controlling and the like.

The image-processing method of the invention may be properly carried out by means of the image-processing apparatus of the invention, at least one of the image forming and erasing through the heating of the reversible thermosensitive recording medium may be carried out by at least one of the image-forming and image-erasing unit, and the other operations may be carried out by means of the other unit.

-Image-Forming Unit and Image-Erasing Unit-

The image-forming unit is the unit in which images are formed through heating the reversible thermosensitive recording medium. The image-erasing unit is the unit in which images are erased through heating the reversible thermosensitive recording medium.

The image-forming unit may be properly selected depending on the application, from a thermal head, laser and the like. These may be used alone or in combination.

The image-erasing unit may be properly selected depending on the application from a hot stamp, ceramic heater, heat roller, heat block, hot blow, thermal head laser irradiation apparatus and the like. Among these, the ceramic heater is preferred. By means of the ceramic heater, the apparatus may be miniaturized, the erasing condition may be stabilized, and images with high contrast may be obtained. The operating temperature of the ceramic heater may be properly selected depending on the application, preferably 110° C. or more, more preferably 112° C. or more, most preferably 115° C. or more, for example.

By means of the thermal head, the apparatus may be minitualized still, in addition, the electric power consumption may be saved, and the power supply may be replaced to a handy type. Further, the performance of image forming and erasing may be combined into one thermal head, thereby the apparatus may be minitualized still more. In the case that the recording and erasing are achieved with one thermal head, once the prior images are erased entirely, then new images may be recorded; alternatively an overwrite type may be provided in which the individual image is erased at variable energy level and new images are recorded. In the overwrite type, the total period for recording and erasing is relatively short, resulting in the speed-up of the recording.

In the case that the reversible thermosensitive recording member (card) with the thermosensitive layer and information memorizing part is utilized, the reading unit and rewriting unit for the memories in the information memorizing part are included in the above-noted apparatus.

The conveying unit may be properly selected depending on the application, provided that the unit performs conveying the reversible thermosensitive recording media successively; a conveying belt, conveying roller, and combination of conveying belt and conveying roller may be exemplified.

The controlling unit may be properly selected depending on the application, provided that the unit performs controlling the respective steps, from a sequencer, computer and the like.

Here, one aspect of the image-processing method through the image-processing apparatus will be explained with reference to FIGS. 5A and 5B. The image-processing apparatus shown in FIG. 5A comprises thermal head 53 as the heating unit, ceramic heater 38, magnetic head 34, conveying rollers 31, 40 and 47.

Figure 5A:
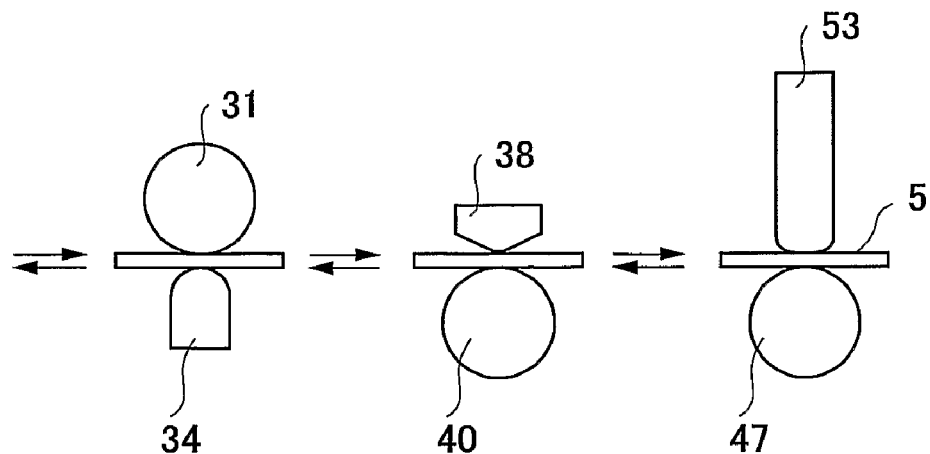
FIG. 5A schematically exemplifies an image-processing apparatus, wherein the image erasing is carried out by a ceramic heater, and the image forming is carried out by a thermal head respectively.

As shown in FIG. 5A, in this image-processing apparatus, the information memorized in the magnetic thermosensitive layer of the reversible thermosensitive recording medium is read by means of the magnetic head initially. Then, heating by means of the ceramic heater erases the images recorded in the thermosensitive layer. Further, the new information processed based on the information read by the magnetic head is recorded in the thermosensitive layer with the thermal head. Thereafter, the information in the magnetic thermosensitive layer is replaced to the new information.

In the image-processing apparatus shown in FIG. 5A, the reversible thermosensitive recording medium 5 in which the magnetic thermosensitive layer is provided on the opposite side of the thermosensitive layer, is conveyed along the conveying root (shown by back-forth arrows) or convened in the reverse direction along the conveying root. The reversible thermosensitive recording medium 5 is subjected to magnetic recording or erasing in the magnetic thermosensitive layer between the magnetic head 34 and the conveying roller 31, and subjected to a heat treatment for erasing images between the ceramic heater 38 and the conveying roller 40, and then images are formed between the thermal head 53 and conveying roller 47, thereafter discharged out of the apparatus. As explained earlier the ceramic heater 38 is preferably set at 110° C. or more, more preferably 112° C. or more, most preferably 115° C. or more. By the way, the rewriting of the magnetic recording may be before or after the image erasing by means of the ceramic heater. In addition, the recording medium is conveyed reversibly after passing between the ceramic heater 38 and conveying roller 40, or after passing between the thermal head 53 and conveying roller 47, if necessary. The duplicated heat treatment by means of ceramic heater 38, and the duplicated printing by means of thermal head 53 may be applied in some instances.

Figure 5B:
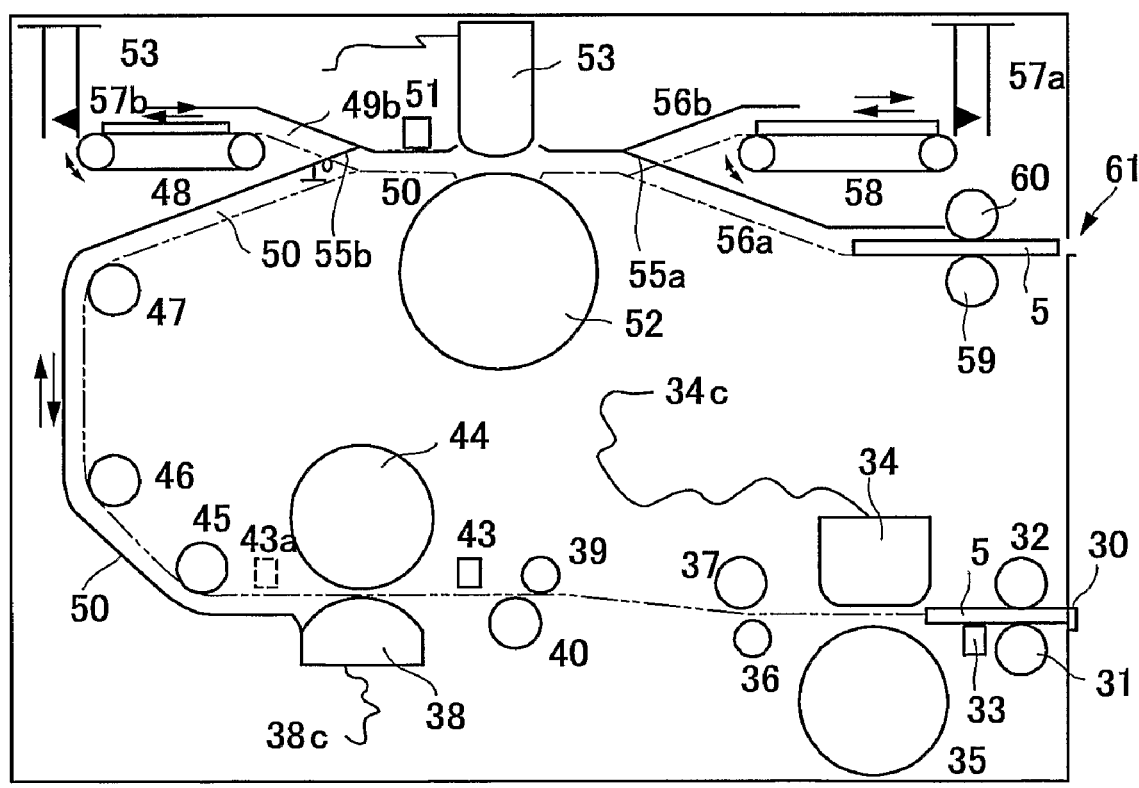
FIG. 5B schematically exemplifies an image-processing apparatus

In the image-processing apparatus shown in FIG. 5B, the reversible thermosensitive recording medium 5, inserted from the entrance 30, progresses along the conveying root 50 shown by alternate long and short dash lines, alternatively progresses reversibly along the conveying root 50 in the apparatus. The reversible thermosensitive recording medium 5, inserted from the entrance 30, is conveyed in the apparatus by means of the conveying roller 31 and the guide roller 32. When it reaches at the predetermined position on the conveying root 50, the existence is detected by means of sensor 33 and controlling device 34c, the magnetic thermosensitive layer is subjected to magnetic recording or erasing between the magnetic head 34 and the platen roller 35, then the reversible thermosensitive recording medium passes between the guide roller 36 and the conveying roller 31 and subsequently between the guide roller 39 and the conveying roller 40, and is subjected to a heat treatment for erasing images between the ceramic heater 38, recognizing the existence by sensor 43 and operating through the ceramic heater controlling device 38c, and platen roller 44, then is conveyed along the conveying root 50 by means of conveying rollers 45, 46 and 47, is subjected to image forming between thermal head 53, recognizing the existence at a certain position by sensor 51 and operating through the thermal head controlling device 53c, and platen roller 52, and is discharged outside from conveying root 56a through exit 61 by means of conveying roller 59 and guide roller 60. By the way the temperature of ceramic heater 38 may be properly set depending on the application as explained earlier, the ceramic heater 38 is preferably set at 110° C. or more, more preferably 112° C. or more, most preferably 115° C. or more.

If desired, the reversible thermosensitive recording medium 5 may be directed to conveying root 56b by switching the conveying root changing device 15a, reversible thermosensitive recording medium 5 is subjected to the heat treatment again between thermal head 53 and platen roller 52 by means of conveying belt 58 which moves reversibly by the action of limit switch 57a which operates by a pressure of reversible thermosensitive recording medium 5, then conveying through conveying root 49b, being connected by changing the conveying root changing device 55b, limit switch 57b and conveying belt 48 in order, and then is discharged outside from conveying root 56a through exit 61 by means of conveying roller 59 and guide roller 60. Further, such blanched conveying root and conveying root changing device may be provided on both sides of the ceramic heater 38. In the case, sensor 43a is preferably provided between platen roller 44 and conveying roller 45.

The invention will be described in more detail below with reference to examples and comparative examples, but the invention is not limited, within the scope of the invention, to the following examples. Wherever "parts" or "%" are mentioned in the following, they are based on weight unless otherwise mentioned.

EXAMPLE 1

[Preparation of Thermosensitive Recording Layer]

| | |
|---|---:|
| Color developer phenol (I) represented by the following formula | 4 parts |

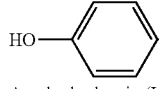
HO—⟨⟩—NHCONH—(CH$_2$)$_{10}$—O—(CH$_2$)$_{21}$CH$_3$

| | |
|---|---:|
| Acrylpolyol resin (LR503 manufactured by Mitsubishi Rayon Co., Ltd., Solid content 50% solution, Hydroxyl value: 64 (KOHmg/g)) | 9 parts |
| Methyl ethyl ketone | 70 parts |

The above-mentioned composition was pulverize and dispersed by means of a ball mill to 1 μm of average particle size. To the resulting dispersion, 1.5 parts of 2-anilino-3-methyl-6-dibutylaminofluoran and 2 parts of adduct-type hexamethylened isocyanate 75% solution in ethyl acetate (Colonate HL, manufactured by Nippon Polyurethane Industry Co., Ltd) was added and stirred well to prepare a coating liquid for thermosensitive recording layer.

Then the coating liquid for thermosensitive recording layer having the above-mentioned composition was coated on a white PET 188 μm thick by means of a wire bar, dried at 100° C. for 2 minutes, followed by heating at 60° C. for 24 hours, thereby a recording layer about 11.0 μm thick was provided. The phenol compound (I) and other similar phenol compounds can be synthesized according to the method described in synthetic examples (Examples 6 to 12) which will be described in more detail later, or similar synthetic methods as these (for example, appropriate modification of solvents to be used or recrystallization solvents).

[Preparation of Protective Layer]

| | |
|---|---:|
| 40% solution of ultraviolet-absorbing polymer (UV-G300, manufactured by Nippon Shokubai Co., Ltd.) | 10 parts |
| Isocyanate compound cross-linking agent (Colonate HX, manufactured by Nippon Polyurethane Industry Co., Ltd.) | 1.4 parts |
| Silicone acrylic resin (GS-1015, manufactured by Toagosei Co., Ltd.) | 0.5 parts |
| Methyl ethyl ketone | 10 parts |

The above-mentioned composition was stirred well to prepare a coating liquid for protective layer.

The coating liquid for protective layer having the above-mentioned composition was coated on the above-noted recording layer by means of a wire bar, was dried at 100° C. for 2 minutes, followed by heating at 60° C. for 24 hours, thereby a protective layer about 3.5 μm thick was provided. As a result, the reversible thermosensitive recording medium according to the invention was prepared.

EXAMPLE 2

A reversible thermosensitive recording medium was prepared in the same manner with Example 1, except that the following compound was used instead of the color developer (I) which was used in Example 1.

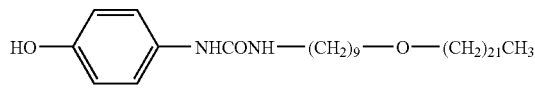

A reversible thermosensitive recording medium was prepared in the same manner with Example 1, except that the following compound was used instead of the color developer (I) which was used in Example 1.

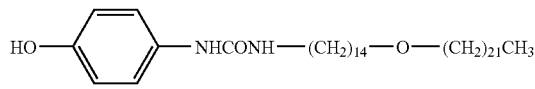

EXAMPLE 4

A reversible thermosensitive recording medium was prepared in the same manner with Example 1, except that the following compound was used instead of the color developer (I) which was used in Example 1.

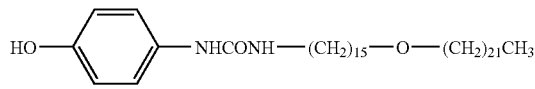

EXAMPLE 5

A reversible thermosensitive recording medium was prepared in the same manner with Example 1 except that the following compound was used instead of the color developer (I) which was used in Example 1.

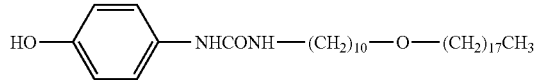

EXAMPLE 6

A reversible thermosensitive recording medium was prepared in the same manner with Example 1 except that the following compound was used instead of the color developer (I) which was used in Example 1.

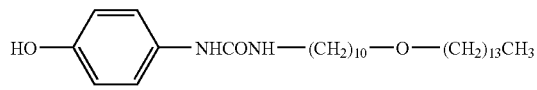

COMPARATIVE EXAMPLE 1

A reversible thermosensitive recording medium was prepared in the same manner with Example 1 except that the following compound was used instead of the color developer (I) which was used in Example 1.

COMPARATIVE EXAMPLE 2

A reversible thermosensitive recording medium was prepared in the same manner with Example 1, except that the following compound was used instead of the color developer (I) which was used in Example 1.

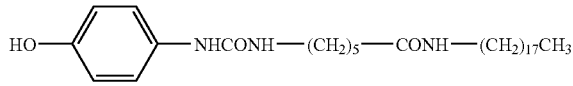

Thus prepared reversible thermosensitive recording media were subjected to the following test.

Test 1: Color Developing Property

Printing was carried out by means of a thermosensitive printing simulator manufactured by Becom Co, Ltd. at the voltage described in Table 1 under a pulse width of 2 msec. color optical density and background optical density were measured by means of Macbeth Densitometer RD914. The results are shown in Table 1.

TABLE 1

| | Color optical density | | | Background |
|---|---|---|---|---|
| | 13 V | 15 V | 17 V | optical density |
| Example 1 | 0.55 | 1.52 | 1.57 | 0.09 |
| Example 2 | 0.77 | 1.78 | 1.79 | 0.07 |
| Example 3 | 0.62 | 1.60 | 1.61 | 0.07 |
| Example 4 | 0.65 | 1.58 | 1.58 | 0.07 |
| Example 5 | 0.61 | 1.73 | 1.79 | 0.07 |
| Example 6 | 0.55 | 1.75 | 1.77 | 0.08 |
| Comp. Example 1 | 0.20 | 0.96 | 1.52 | 0.10 |
| Comp. Example 2 | 0.17 | 0.23 | 0.88 | 0.12 |

Test 2: Color Erasing Property

As in test 1, printing was carried out by means of the thermosensitive printing device (manufactured by Becom Corp.) at the voltage described in the Table 2, heated by means of a heat slope tester (manufactured by Toyo Seiki Kogyo Co., Ltd.) for 1 second at 1 kgf/cm², and then the density before and after erasing was measured in the same way as in Test 1. The results are shown in Table 2.

Note that the conditions of the voltage during printing and erasing temperature were suitably selected depending on the coloring sensitivity and color erasing property.

TABLE 2

|  | Printing voltage | Image density | Erasing temperature | Erasing optical density |
|---|---|---|---|---|
| Example 1 | 15 V | 1.52 | 110° C. | 0.09 |
| Example 2 | 15 V | 1.78 | 110° C. | 0.08 |
| Example 3 | 15 V | 1.61 | 110° C. | 0.08 |
| Example 4 | 15 V | 1.53 | 110° C. | 0.08 |
| Example 5 | 15 V | 1.71 | 110° C. | 0.08 |
| Example 6 | 15 V | 1.77 | 110° C. | 0.08 |
| Comp. Example 1 | 17 V | 1.52 | 130° C. | 0.13 |
| Comp. Example 2 | 20 V | 1.50 | 160° C. | 0.14 |

Test 3: Image Preservability

Printed image obtained in Test 2 was preserved for 24 hours under the dry condition of 60° C. Densities before and after preservation were measured in the same way as in Test 1 and image retention rate was then calculated according to the following equation;

image retention rate (%)=image density after preservation−background optical density after preservation/image density before preservation background optical density before preservation)×100

TABLE 3

|  | Image preservability |
|---|---|
| Example 1 | 81% |
| Example 2 | 78% |
| Example 3 | 90% |
| Example 4 | 92% |
| Example 5 | 60% |
| Example 6 | 51% |
| Comp. Example 1 | 8% |
| Comp. Example 2 | 15% |

EXAMPLE 7

—Synthesis of Phenol Compound (I) which was Used in Example 1—

Figure 6:
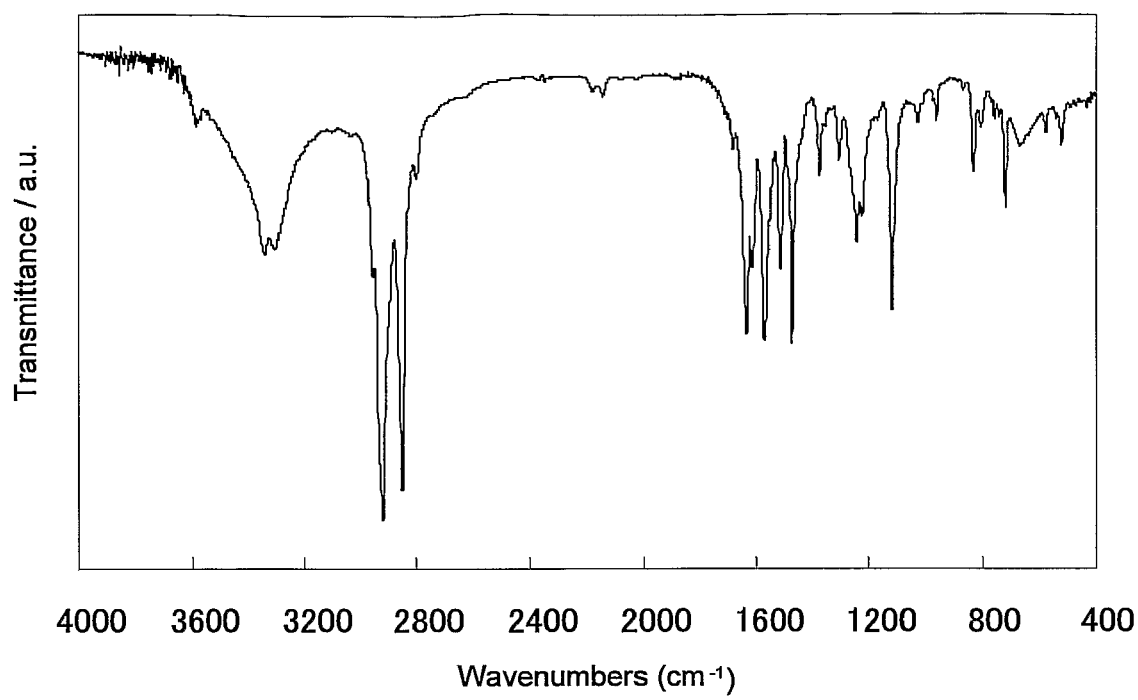
FIG. 6 shows an IR absorption spectrum of the phenol compound (I) which was used in Examples 1 and 7.

To 300 ml of anhydrous toluene, 12.0 g of 10-docosanoxy decyl isocyanate was added and stirred at room temperature. To the resulting solution 2.7 g of p-aminophenol was added and stirred under reflux at 110° C. for 2 hours. Thereafter, the solution was brought back to a room temperature of 25° C., to the resulting liquid, 20% hydrochloric acid and ethanol were added, solids were filtered off, washed with ethyl acetate, and recrystallized with methyl ethyl ketone to thereby obtain the object. At this time the yield of the object was 79%. The melting point of the object and the results of the elemental analysis thereof are shown in Table 4. The object had a melting point of 123° C. FIG. 6 shows the infrared absorption spectrum of the object. Absorption in the vicinity of 1650 $cm^{-1}$ to 1450 $cm^{-1}$, which is specific to a urea bond and absorption in the vicinity of 1100 $cm^{-1}$, which is specific to ether bond (—O—) are found. From the melting point, elemental analysis, and infrared absorption spectrum the obtained substance was confirmed to be the object.

EXAMPLE 8

-Synthesis of Phenol Compound which was in Example 2-

Figure 7:
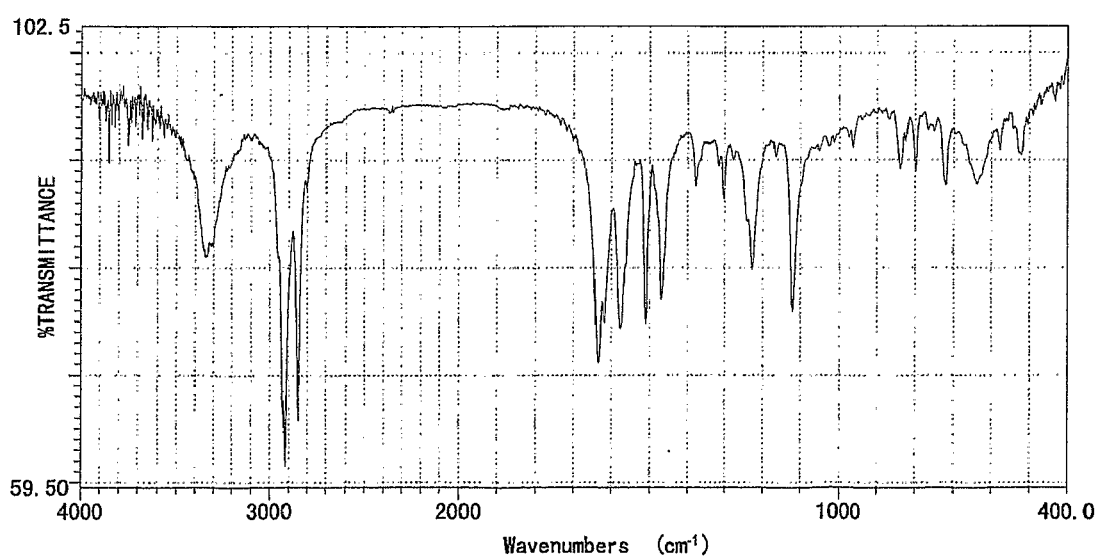
FIG. 7 shows an IR absorption spectrum of the phenol compound which was used in Examples 2 and 8.

To 150 ml of anhydrous toluene, 5.5 g of 9-docosanoxy nonyl isocyanate was added and stirred at room temperature. To the resulting solution 1.3 g of p-aminophenol was added and stirred under reflux at 110° C. for 2 hours. Thereafter the solution was brought back to a room temperature of 25° C., solids were filtered off, washed with acetone, and recrystallized with methyl ethyl ketone to thereby obtain 6.2 g of the object. At this time, the yield of the object was 93%. The melting point of the object and the results of the elemental analysis thereof are shown in Table 4. FIG. 7 shows the infrared absorption spectrum of the object. From the elemental analysis and infrared absorption spectrum, the obtained substance was confirmed to be the object.

EXAMPLE 9

—Synthesis of Phenol Compound which was in Example 3—

Figure 8:
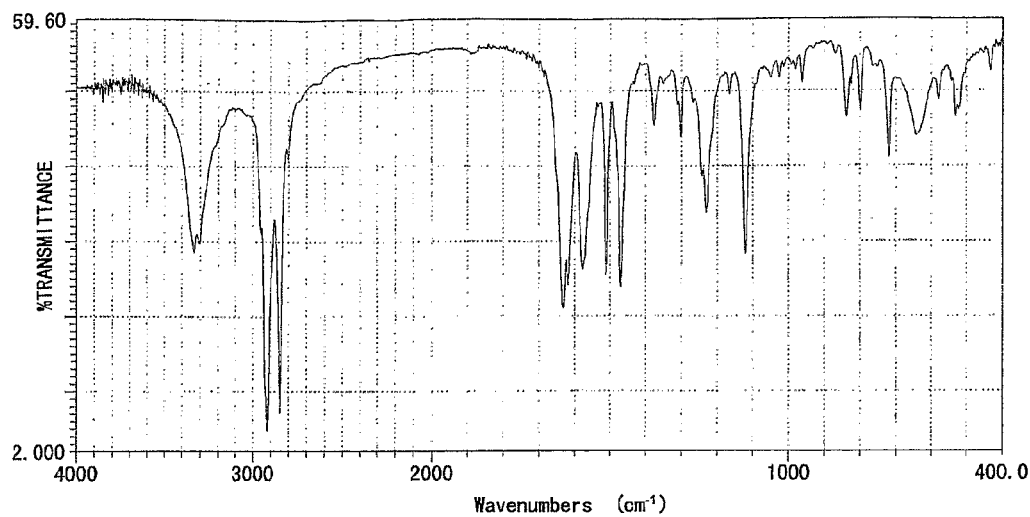
FIG. 8 shows an IR absorption spectrum of the phenol compound which was used in Examples 3 and 9.

To 150 ml of anhydrous toluene, 4.8 g of 14-docosanoxy tetradecyl isocyanate was added and stirred at room temperature. To the resulting solution, 0.98 g of p-aminophenol was added and stirred under reflux at 110° C. for 2 hours. Thereafter, the solution was brought back to a room temperature of 25° C., solids were filtered off, washed with acetone, and recrystallized with methyl ethyl ketone to thereby obtain 5.5 g of the object. At this time, the yield of the object was 96%. The melting point of the object and the results of the elemental analysis thereof are shown in Table 4. FIG. 8 shows the infrared absorption spectrum of the object. From the elemental analysis and infrared absorption spectrum, the obtained substance was confirmed to be the object.

EXAMPLE 10

-Synthesis of Phenol Compound which was in Example 4-

Figure 9:
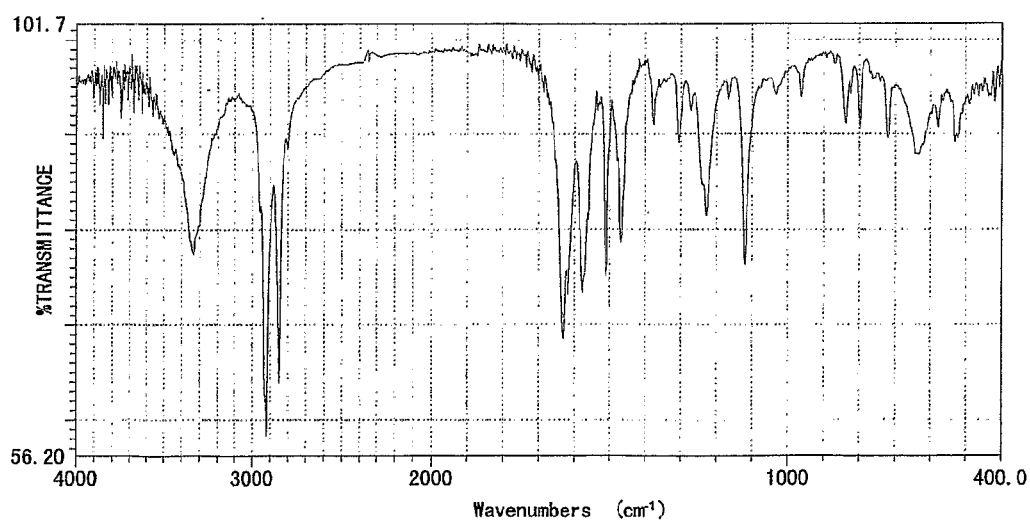
FIG. 9 shows an IR absorption spectrum of the phenol compound which was used in Examples 4 and 10.

To 200 ml of anhydrous toluene, 6.1 g of 15-docosanoxy pentadecyl isocyanate was added and stirred at room temperature. To the resulting solution, 1.2 g of p-aminophenol was added and stirred under reflux at 110° C. for 2 hours. Thereafter the solution was brought back to a room temperature of 25° C., solids were filtered off, washed with acetone, and recrystallized with methyl ethyl ketone to thereby obtain 6.6 g of the object. At this time, the yield of the object was 91%. The melting point of the object and the results of the elemental analysis thereof are shown in Table 4. FIG. 9 shows the infrared absorption spectrum of the object. From the elemental analysis and infrared absorption spectrum, the obtained substance was confirmed to be the object.

EXAMPLE 11

-Synthesis of Phenol Compound which was in Example 5-

Figure 10:
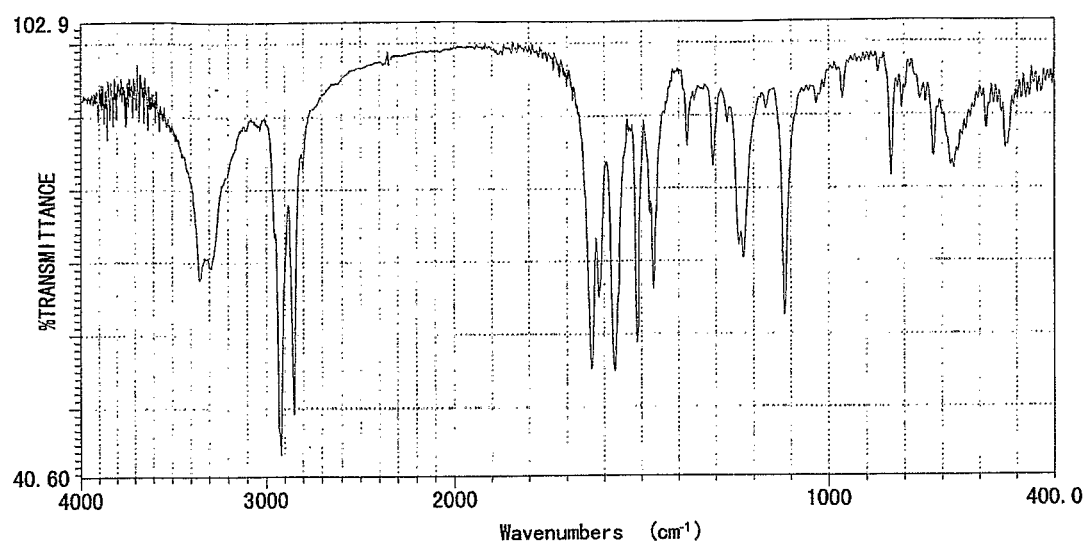
FIG. 10 shows an IR absorption spectrum of the phenol compound which was used in Examples 5 and 11.

To 250 ml of anhydrous toluene, 7.4 g of 10-stearoxy decyl isocyanate was added and stirred at room temperature. To the resulting solution, 1.9 g of p-aminophenol was added and stirred under reflux at 110° C. for 2 hours. Thereafter, the solution was brought back to a room temperature of 25° C., solids were filtered off, washed with acetone, and recrystallized with methyl ethyl ketone to thereby obtain 7.1 g of the object. At this time, the yield of the object was 77%. The melting point of the object and the results of the elemental analysis thereof are shown in Table 4. FIG. 10 shows the infrared absorption spectrum of the object. From the elemental analysis and infrared absorption spectrum, the obtained substance was confirmed to be the object

EXAMPLE 12

-Synthesis of Phenol Compound which was in Example 6-

Figure 11:
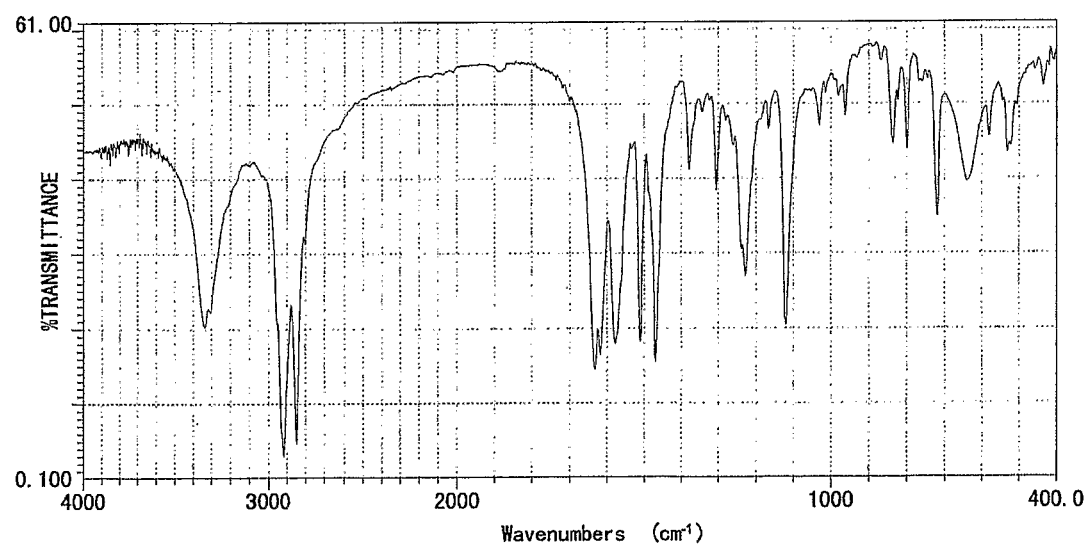
FIG. 11 shows an IR absorption spectrum of the phenol compound which was used in Examples 6 and 12.

To 300 ml of anhydrous toluene, 14.1 g of 10-myristoxy decyl isocyanate was added and stirred at room temperature. To the resulting solution 4.1 g of p-aminophenol was added and stirred under reflux at 110° C. for 2 hours. Thereafter the solution was brought back to a room temperature of 25° C., solids were filtered off, washed with acetone, and recrystallized with methyl ethyl ketone to thereby obtain 12.6 g of the object. At this time, the yield of the object was 70%. The melting point of the object and the results of the elemental analysis thereof are shown in Table 4. FIG. 11 shows the infrared absorption spectrum of the object. From the elemental analysis and infrared absorption spectrum, the obtained substance was confirmed to be the object.

TABLE 4

| | Melting point (° C.) | Elemental analysis | |
|---|---|---|---|
| | | Theoretical value | Observed value |
| Example 7 | 123 | C, 75.92; H, 11.76; N, 4.54 | C, 75.95; H, 11.82; N, 4.53 |
| Example 8 | 124 | C, 75.69; H, 11.70; N, 4.65 | C, 75.45; H, 11.82; N, 4.62 |
| Example 9 | 127 | C, 76.73; H, 11.98; N, 4.16 | C, 76.74; H, 12.10; N, 4.00 |
| Example 10 | 126 | C, 76.91; H, 12.03; N, 4.08 | C, 76.93; H, 12.20; N, 4.05 |
| Example 11 | 124 | C, 74.95; H, 11.50; N, 4.99 | C, 74.97; H, 11.54; N, 5.01 |
| Example 12 | 122 | C, 73.76; H, 11.18; N, 5.55 | C, 73.40; H, 11.14; N, 5.59 |

EXAMPLE 13

A reversible thermosensitive recording medium was prepared in the same manner with Example 1, except that the acrylpolyol resin (Solid content 50%, Hydroxyl value: 108 (KOHmg/g)) was used as the acrylpolyol resin.

EXAMPLE 14

A reversible thermosensitive recording medium was prepared in the same manner with Example 1, except that the acrylpolyol resin (Solid content 50%, Hydroxyl value: 200 (KOHmg/g)) was used as the acrylpolyol resin.

EXAMPLE 15

A reversible thermosensitive recording medium was prepared in the same manner with Example 1, except that the acrylpolyol resin (Sold content 50%, Hydroxyl value: 300 (KOHmg/g)) was used as the acrylpolyol resin.

EXAMPLE 16

A reversible thermosensitive recording medium was prepared in the same manner with Example 1, except that the 2-anilino-3-methyl-6-(3-ethoxypropyl)ethylaminofluoran (Black 500 manufactured by Yamada Chemical Co. Ltd.) was used instead of the 2-anilino-3-methyl-6-dibutylaminofluoran.

EXAMPLE 17

A reversible thermosensitive recording medium was prepared in the same manner with Example 1, except that the acrylpolyol resin (Solid content 50%, Hydroxyl value: 200 (KOHmg/g)) was used, and further the 2-anilino-3-methyl-6-(3-ethoxypropyl)ethylaminofluoran (Black 500 manufactured by Yamada Chemical Co., Ltd.) was used instead of the 2-anilino-3-methyl-6-dibutylaminofluoran.

EXAMPLE 18

A reversible thermosensitive recording medium was prepared in the same manner with Example 17, except that, in Example 17, the following compound was used instead of the color developer (I).

Test: Color Erasing Property 2

As in test 1, printing was carried out by means of the thermosensitive printing device (manufactured by Becom Corp.) at a voltage of 15, heated by means of the heat slope tester (manufactured by Toyo Seiki Kogyo Co. Ltd.) for 0.4 seconds or 0.2 seconds at 1 kg cm$^2$, and then the density before and after erasing was measured in the same way as in Test 1. The results are shown in Table 5.

TABLE 5

| | Background optical density | Image density | Erasing optical density | |
|---|---|---|---|---|
| | | | 0.4 seconds | 0.2 seconds |
| Example 1 | 0.09 | 1.52 | 0.12 | 0.17 |
| Example 13 | 0.09 | 1.50 | 0.11 | 0.14 |
| Example 14 | 0.09 | 1.58 | 0.09 | 0.11 |
| Example 15 | 0.09 | 1.52 | 0.09 | 0.12 |
| Example 16 | 0.09 | 1.53 | 0.09 | 0.11 |
| Example 17 | 0.09 | 1.59 | 0.09 | 0.09 |
| Example 18 | 0.09 | 1.62 | 0.09 | 0.09 |

INDUSTRIAL APPLICABILITY

The reversible thermosensitive recording medium of the invention are applied for prepaid card, point card and also credit card, when formed into a card-like shape. The recording medium formed into a sheet-like shape may be applied for normal document, instructing letter for process management, or the like, owing to the wider printable area than the card-like size. Accordingly, the reversible thermosensitive recording medium of the invention may be applied in a wide range for stickers, e.g. on a entry/exit ticket, container for frozen foods, industrial product, various chemical container; and applied for large screens or various displays, e.g. for physical distribution management, production process management.

The invention claimed is:

1. A reversible thermosensitive recording medium comprising:
a support; and
a thermosensitive recording layer thereon,
wherein the thermosensitive recording layer comprises an electron-donating coloring compound and an electron-accepting compound, and the thermosensitive recording layer can form a developed condition and an erased condition depending on at least one of the difference of heating temperatures and the difference of cooling rates following to heating, and wherein the electron-accepting compound comprises a phenol compound represented by the General Formula (1):

General Formula (1)

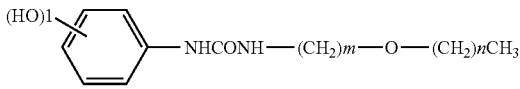

where, in the General Formula (1), "1" represents an integer of 1 to 3, "m" represents an integer of 1 or more, and "n" represents an integer of 7 or more.

2. The reversible thermosensitive recording medium according to claim 1, wherein the electron-accepting compound is a phenol compound represented by the following General Formula (2):

General Formula (2)

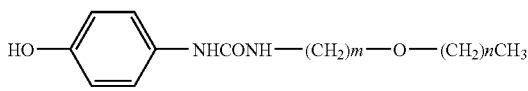

where, in the General Formula (2), "m" represents an integer of 1 or more, and "n" represents an integer of 7 or more.

3. The reversible thermosensitive recording medium according to claim 1, wherein the "m" is an integer of 1 or more and the "n" is an integer of 11 to 29.

4. The reversible thermosensitive recording medium according to claim 3, wherein the "m" is an integer of 1 or more and the "n" is an integer of 14 to 22.

5. The reversible thermosensitive recording medium according to claim 1, wherein the thermosensitive recording layer further comprises a crosslinked resin.

6. The reversible thermosensitive recording medium according to claim 5, wherein the crosslinked resin is crosslinked with an isocyanate compound.

7. The reversible thermosensitive recording medium according to claim 1, wherein the electron-donating coloring compound is a leuco dye, and wherein the leuco dye has an alkoxyalkyl group in an amino side chain thereof.

8. The reversible thermosensitive recording medium according to claim 1, further comprising a protective layer on the thermosensitive recording layer, wherein the protective layer comprises a crosslinked resin.

9. The reversible thermosensitive recording medium according to claim 1, wherein the reversible thermosensitive recording medium is formed into one of a card, label, sheet, or roll configurations.

10. A reversible thermosensitive recording label comprising:

a reversible thermosensitive recording medium; and
one of an adhesive layer and a tacky layer,
wherein one of the adhesive layer and the tacky layer is disposed on an exposed surface of the reversible thermosensitive recording medium opposite to an exposed surface on which an image is formed, wherein the reversible thermosensitive recording medium comprises a support and a thermosensitive recording layer thereon, wherein the reversible thermosensitive recording layer comprising an electron- donating color compound and an electron-accepting compound and reversibly changes the color depending on temperatures, and the reversible thermosensitive recording layer can form a developed condition and an erased condition depending on at least one of the differences of heating temperatures and the differences of cooling rates following to heating, and wherein the electron-accepting compound comprises a phenol compound represented by the General Formula (1):

General Formula (1)

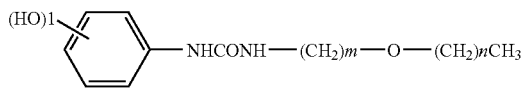

where, in the General Formula (1), "1" represents an integer of 1 to 3, "m" represents an integer of 1 or more, and "n" represents an integer of 7 or more.

11. A reversible thermosensitive recording member comprising:

an information-memorizing part; and
a reversible displaying part,
wherein the reversible displaying part comprises the reversible thermosensitive recording medium, wherein the reversible thermosensitive recording medium comprises a support and a thermosensitive recording layer thereon, wherein the reversible thermosensitive recording layer comprising an electron-donating color compound and an electron-accepting compound and reversibly changes the color depending on temperatures, and the reversible thermosensitive recording layer can form a developed condition and an erased condition depending on at least one of the differences of heating temperatures and the differences of cooling rates following to heating, and wherein the electron-accepting compound comprises a phenol compound represented by the General Formula (1):

General Formula (1)

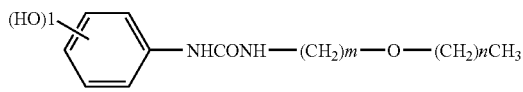

where, in the General Formula (1), "1" represents an integer of 1 to 3, "m" represents an integer of 1 or more, and "n" represents an integer of 7 or more.

12. The reversible thermosensitive recording member according to claim 11, wherein the information-memorizing part and the reversible displaying part are integrated.

13. The reversible thermosensitive recording member according to claim 11, wherein the information-memorizing part is selected from the group consisting of a magnetic thermosensitive layer, a magnetic stripe, an IC memory, an optical memory, a hologram, a RF-ID tag card, a disc, a disc cartridge and a tape cassette.

14. An image-processing apparatus comprising: at least one of an image-forming unit and an image-erasing unit, wherein images are formed on a reversible thermosensitive recording medium by heating the reversible thermosensitive recording medium in the image-forming unit, images are erased from the reversible thermosensitive recording medium by heating the reversible thermosensitive recording medium in the image-erasing unit, and wherein the reversible thermosensitive recording medium comprises a support and a thermosensitive recording layer thereon, wherein the reversible thermosensitive recording layer comprising an electron-donating color compound and an electron-accepting compound and reversibly changes the color depending on temperatures, and the reversible thermosensitive recording layer can form a developed condition and an erased condition depending on at least one of the differences of heating temperatures and the differences of cooling rates following to heating, and wherein the electron-accepting compound comprises a phenol compound represented by the General Formula (1):

General Formula (1)

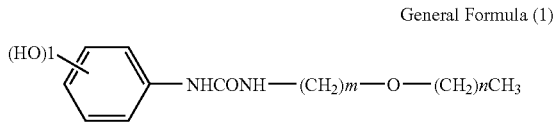

where, in the General Formula (1), "l" represents an integer of 1 to 3, "m" represents an integer of 1 or more, and "n" represents an integer of 7 or more.

15. The image-processing apparatus according to claim 14, wherein the image-forming unit has one of a thermal head and a laser irradiation apparatus.

16. The image-processing apparatus according to claim 14, wherein the image-erasing unit comprises one selected from the group consisting of a thermal head, a ceramic heater, a heat roll, a hot stamp, a heat block and a laser irradiation apparatus.

17. An image-processing method comprising: at least one of forming images on a reversible thermosensitive recording medium by heating the reversible thermosensitive recording medium, and erasing images from a reversible thermosensitive recording medium by heating the reversible thermosensitive recording medium, wherein the reversible thermosensitive recording medium comprises a support and a thermosensitive recording layer thereon, wherein the reversible thermosensitive recording layer comprising an electron-donating color compound and an electron-accepting compound and reversibly changes the color depending on temperatures, and the reversible thermosensitive recording layer can form a developed condition and an erased condition depending on at least one of the differences of heating temperatures and the differences of cooling rates following to heating, and wherein the electron-accepting compound comprises a phenol compound represented by the General Formula (1):

General Formula (1)

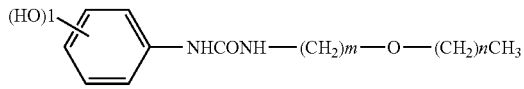

where, in the General Formula (1), "l" represents an integer of 1 to 3, "m" represents an integer of 1 or more, and "n" represents an integer of 7 or more.

18. A phenol compound, which is represented by the following General Formula (1):

General Formula (1)

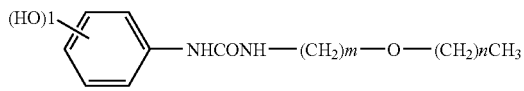

where, in the General Formula (1), "l" represents an integer of 1 to 3, "m" represents an integer of 1 or more, and "n" represents an integer of 7 or more.

19. The phenol compound according to claim 18, which is represented by the following General Formula (2):

General Formula (2)

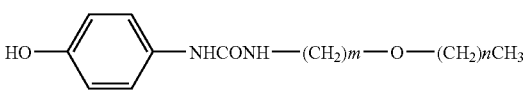

where, in the General Formula (2), "m" represents an integer of 1 or more, and "n" represents an integer of 7 or more.

20. The phenol compound according to claim 18, wherein the "m" is an integer of 1 or more, and the "n" is an integer of 11 to 29.

21. The phenol compound according to claim 20, wherein the "m" is an integer of 1 or more and the "n" is an integer of 14 to 22.

* * * * *

UNITED STATES PATENT AND TRADEMARK OFFICE
CERTIFICATE OF CORRECTION

| | |
|---|---|
| PATENT NO. | : 7,456,132 B2 |
| APPLICATION NO. | : 11/572058 |
| DATED | : November 25, 2008 |
| INVENTOR(S) | : Yamamoto et al. |

It is certified that error appears in the above-identified patent and that said Letters Patent is hereby corrected as shown below:

On the title page, Item (30), The Foreign Application Priority Data has been omitted. Item (30) should read:

--(30) Foreign Application Priority Data

July 13, 2004 (JP)...............................2004-206011--

On the title page, Item (54) and Column 1, the title is incorrect. Item (54) and Column 1 should read:

--(54) PHENOL COMPOUND, REVERSIBLE THERMOSENSITIVE RECORDING MEDIUM, REVERSIBLE THERMOSENSITIVE RECORDING LABEL, REVERSIBLE THERMOSENSITIVE RECODING MEMBER, IMAGE-PROCESSING APPARATUS AND IMAGE-PROCESSING METHOD--

Signed and Sealed this

Tenth Day of February, 2009

JOHN DOLL
*Acting Director of the United States Patent and Trademark Office*